US007049099B2

(12) United States Patent
Wakamiya

(10) Patent No.: US 7,049,099 B2
(45) Date of Patent: May 23, 2006

(54) RECOMBINANT HUMAN MANNAN-BINDING PROTEINS AND PRODUCING METHOD OF THE SAME

(75) Inventor: Nobutaka Wakamiya, Ibaraki (JP)

(73) Assignee: FUSO Pharmaceutical Industries, Ltd., Osaka (JP)

(*) Notice: Subject to any disclaimer, the term of this patent is extended or adjusted under 35 U.S.C. 154(b) by 282 days.

(21) Appl. No.: 10/054,536

(22) Filed: Jan. 22, 2002

(65) Prior Publication Data

US 2003/0162248 A1   Aug. 28, 2003

Related U.S. Application Data

(62) Division of application No. 09/600,950, filed on Sep. 8, 2000, now abandoned.

(30) Foreign Application Priority Data

Jan. 23, 1998  (JP) .................................. 10-11864

(51) Int. Cl.
*C12P 21/04* (2006.01)
*C12N 15/00* (2006.01)
*C12N 15/09* (2006.01)
*C12N 5/10* (2006.01)

(52) U.S. Cl. .................. 435/69.6; 435/320.1; 435/69.3; 435/69.1; 435/70.1; 435/362; 435/358

(58) Field of Classification Search ............... 435/69.1, 435/69.3, 69.6, 70.1, 362, 358, 320.1
See application file for complete search history.

(56) References Cited

U.S. PATENT DOCUMENTS 5,270,199 A    12/1993  Ezekowitz ............... 435/240.2

FOREIGN PATENT DOCUMENTS

| JP | 2-504581 | 12/1990 |
|---|---|---|
| WO | WO 8901519 | 2/1989 |
| WO | WO 98/55614 | 12/1998 |

OTHER PUBLICATIONS

Ma et al. J. Biochem. 122: 810-818, Oct. 1997.*
Otani et al. Nippon Men'eki Gokkai Soaki, Gakujutsu Shukai Kiroku 27: 182, Sep. 29, 1997 (Original & English translation).*
Tan et al., "Improvements on the purification of mannan-binding lectin and demonstration of its CA2+-independent association with a C1s-like serine protease," *Biochem. J. 391*, 329-332 (1996).
Epstein, et al., "The collectins in innate immunity," *Current Opinion in Immunology*, 8:29-35 (1996).
Ezekowitz, R.A.B. et al.; "A Human Mannose-binding Protein is an acute-phase Reactant that Shares Sequence Homology with Other Vertebrate Lectins," *J. Exp. Med.*, 167:1034-1046 (Mar. 1988).

Ezekowitz, R.A.B. et al., "Mannose-binding protein and susceptibility to chronic hepatitis B infection," *The Lancet*, 348:1396-1397(Nov. 1996).
Fujita, T., "Complement activation and Lectin Pathway," *Rinsho-Meneki*, 29(3):405-410 (1997). (Japanese with English abstract translation).
Garred, et al., Susceptibility to HIV infection and progression of AIDS in relation to variant alleles of mannose-binding lectin,: *The Lancet*, 349:236-240 (Jan. 1997).
Kawai, et al., "Cloning and characterization of a cDNA encoding bovine mannan-binding protein," *Gene*, 186(2);161-165 (Feb. 1997).
Kuruta, H., "Structure and Function of Mannan-Binding Proteins Isolated from Human Liver and Serum," *J. Biochem.*, 115(6);1148-1154 (1994).
Lim, et al., "Primary Structure of Bovine Collectin-43 (CL-43) Comparison with conglutinin and lung surfactant protein-D," *J. Biol. Chem.*, 269(16);11820-11824 (Apr. 1994).
Lipscombe, et al., "Mutations in the Human Mannose-Binding Gene: Frequencies in several population groups," *European Journal of Human Genetics*, 4(1);13-19 (1996).
Lu, et al., "Purification, characterization and cDNA clonning of human lung surfactant protein D," *Biochem. J.*, 284:795-802 (1992).
Malhortra, et al., "Interaction of C1q receptor with lung surfactant protein A", *Eur. J. Immun.*, 22:1437-1445 (1992).
Malhortra, et al., "Glysosylation changes of IgG associated with rheumatoid arthritis can activate complement via the mannose-binding protein," *Nature Medicine*, 1(3);237-243 (Mar. 1995).
Matsuda, et al., "Involvement of Mannan Binding Protein with crisis and progression of IgA nephrosis," *Journal of Nephrology Association of Japan*, 39(3):235 (1997). (Japanese with English abstract translation).
Nepomuceno, et al., "cDNA Cloning and Primary Structure Analysis of C1qR$_p$), the Human Cl1/MBL/SPA Receptor That Mediates Enhanced Phagocytosis *in Vitro*," *Immunity*, 6(2):119-129 (Feb. 1997).
Sastry, et al., "The Human Mannose-binding Protein Gene: Exon Structure Reveals its Evolutionary relationship to a Human Pulmonary Surfactant Gene and Localization to Chromosome 10," *J. Exp. Med.*, 170:1175-1189 (1989).

(Continued)

Primary Examiner—S. Devi
(74) Attorney, Agent, or Firm—Marshall, Gerstein & Borun LLP

(57) ABSTRACT

Recombinant Human Mannan-Binding Proteins (rhMBP) having physiological activities which are substantially identical to those offered by Human Mannan-Binding Proteins (hMBP), as well as, in particular, a production system for homogenously producing rhMBP having the specific peaks at the molecular weight of 1,000~1,300 kDa determined by absorbance (280 nm) in Gel-Filtration Chromatography are provided.

3 Claims, 22 Drawing Sheets

OTHER PUBLICATIONS

Sumiya, et al., "Molecular basis of opsonic defect in immunodeficient children," *Lancet*, 337:1569-1570 (Jun. 1991).

Sumiya, et al., "Mannose-binding protein, genetic variant and the ristk of infection," *Q. J. Med.*, 89:723-726 (1996).

Super, et al., "Association of Low Levels of Mannan-binding Protein with a Common Defect of Opsonisation," *Lancet*,2: 1236-1239 (Nov. 1989).

Suzuki et al., :Cloning and Sequencing of a cDNA Coding for Bovine Conglutinin, *Biochem Biophys Res Commun*, 191/2, 335-342 (1993).

Suzuki et al., "Characterization of Recombinant Bovine Conglutinin Expressed in a Mammalian Cell," *Biochem Biophys Res Commun*, 238, 856-863 (1997).

Taylor, et al., "Structure and evolutionary origin of the gene encoding a human serum mannose-binding protein," *Biochem J.*, 262: 763-771 (1989).

Thomas, et al., "Mutation of gene for mannose-binding protein associated with chronic hepatitis B viral infection," *Lancet*,348: 14176-1419 (Nov. 1996).

Uemura, et al., "Correlation Between Structure and Function of Calcium Dependence Animal Lectin on Host Defence," *Jikken-Igaku*, 13(18) (1995). (Japanese with English abstract translation).

Wakamiya, et al., "The Mannose Binding Protein and Conglutinin in Bovine Serum Have an Antiviral Activity Against Influenza Virus," *Glycoconjugate Journal*, 8:235 (1991).

Wakamiya, et al., "Isolation and Characterization of Conglutinin as an Influenza A Virus Inhibitor," *Biochem. Biophys, Res. Comm.*, 187: 1270-1278 (Sep. 1992).

Wakamiya, et al., "Anti-Viral Activity by Collectin," *Rinsho-Meneki*, 29(4); 508-513 (1997). (Japanese with English abstract translation).

Eda, et al., "Characterization of Truncated Human Mannan-Binding Protein (MBP) Expressed in *Escherichia Coli*," *Biosci. Biotechnol. Biochem.*, 62(7): 1326-1331 (1998).

* cited by examiner

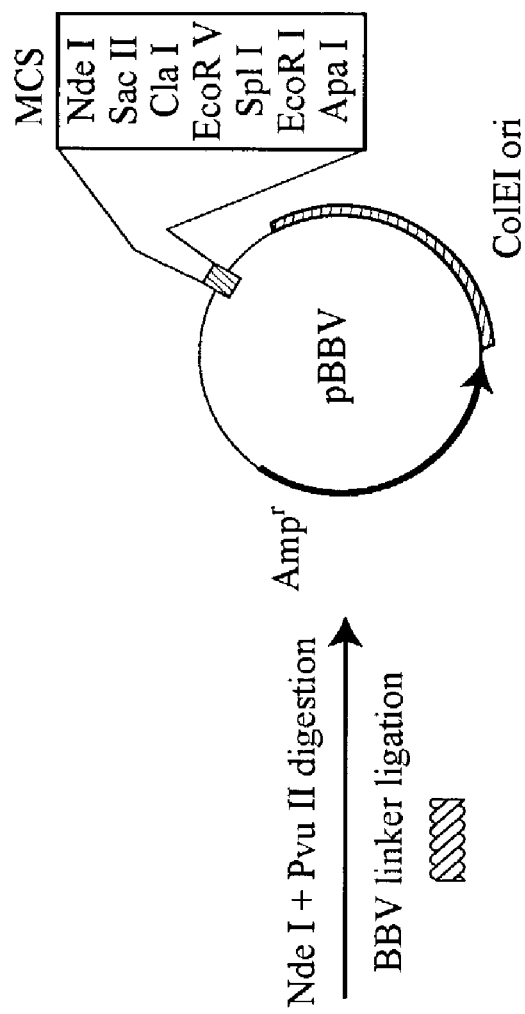
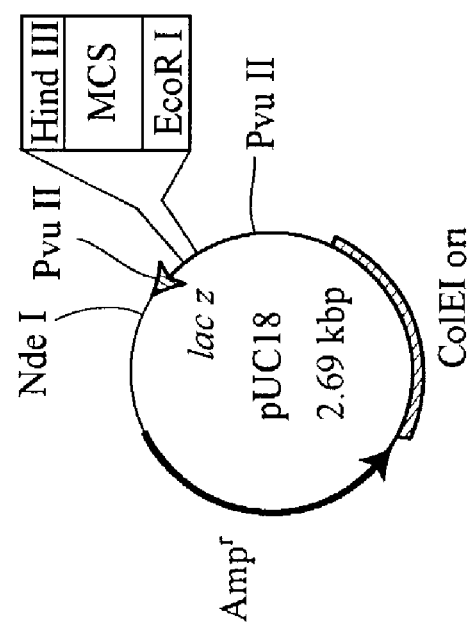
FIG. 2

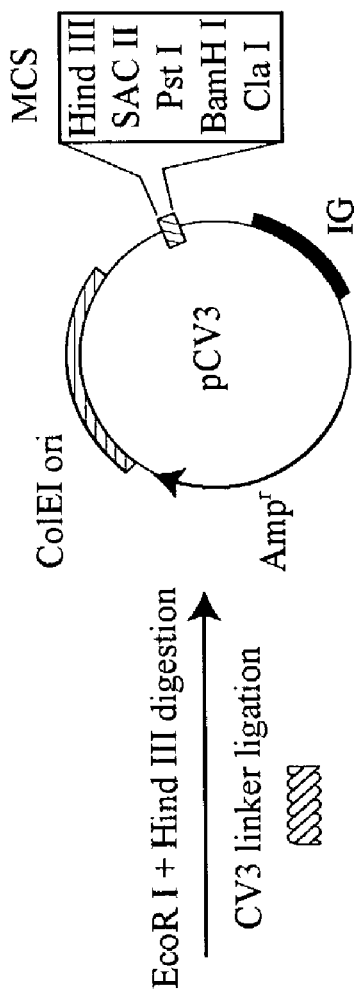
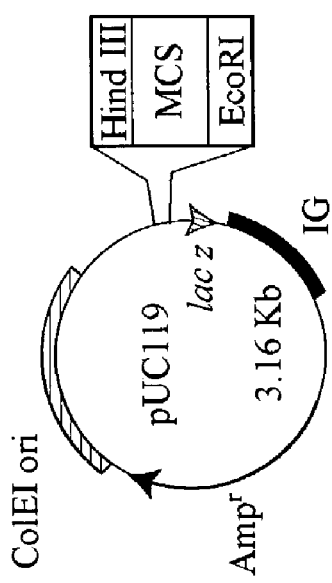
FIG. 3

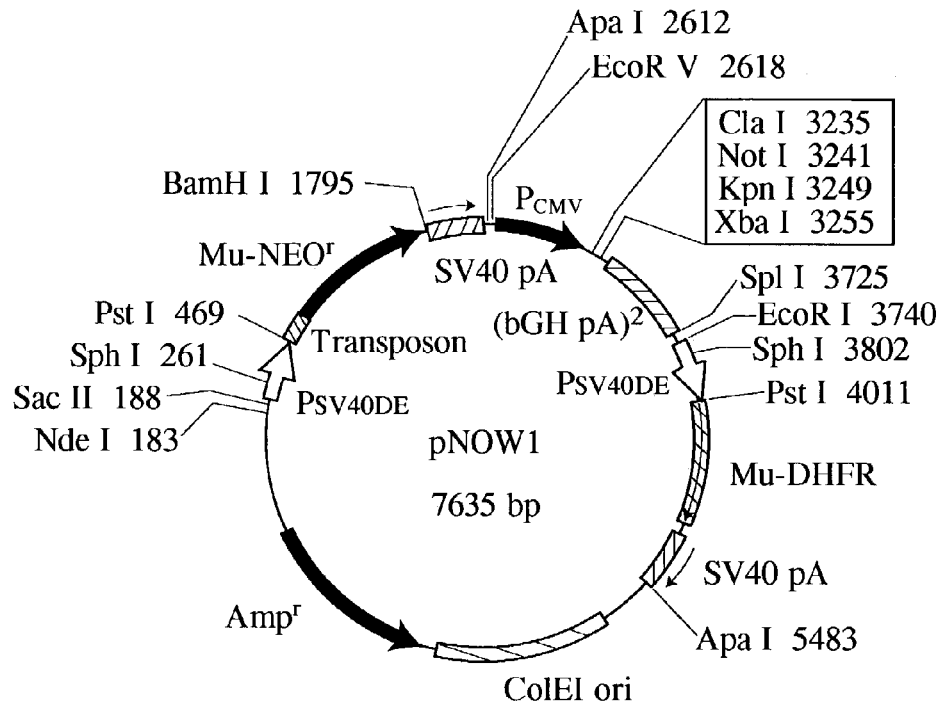

| Ampr | Ampicillin Resistance Gene |
| --- | --- |
| (bGHpA)² | Bovine Growth Hormone Polyadenylation Signal |
| ColEI | Escherichia coli Replication Origin |
| Mu-DHFR | DHFG Gene introduced thereinto Mutation |
| MU-NEOr | Neomycin Resistance Gene introduced thereinto Mutation |
| Pcmv | Human Cytomegalovirus Major Immediate-Early Antigen Promoter |
| PSV40DE | Attenuated SV40 Promoter (including SV40 Replication Origin) |
| SV40pA | SV40 Polyadenylation Signal |
| Transposon | Transposon Sequence |

FIG. 11

SEQUENCE LISTING

```
<160> NUMBER OF SEQ ID NOS: 28

<210> SEQ ID NO 1
<211> LENGTH: 3605
<212> TYPE: DNA
<213> ORGANISM: Homo sapiens
<220> FEATURE:
<221> NAME/KEY: CDS
<222> LOCATION: (66)..(809)
<220> FEATURE:
<221> NAME/KEY: mat_peptide
<222> LOCATION: (126)..(809)

<400> SEQUENCE: 1
ggtaaatatg tgttcattaa ctgagattaa ccttccctga gttttctcac accaaggtga        60 ggacc atg tcc ctg ttt cca tca ctc cct ctc ctt ctc ctg agt atg gtg       110
      Met Ser Leu Phe Pro Ser Leu Pro Leu Leu Leu Leu Ser Met Val
          -20             -15                 -10 gca gcg tct tac tca gaa act gtg acc tgt gag gat gcc caa aag acc         158
Ala Ala Ser Tyr Ser Glu Thr Val Thr Cys Glu Asp Ala Gln Lys Thr
 -5              -1   1               5                  10 tgc cct gca gtg att gcc tgt agc tct cca ggc atc aac ggc ttc cca         206
Cys Pro Ala Val Ile Ala Cys Ser Ser Pro Gly Ile Asn Gly Phe Pro
                 15                  20                  25 ggc aaa gat ggg cgt gat ggc acc aag gga gaa aag ggg gaa cca ggc         254
Gly Lys Asp Gly Arg Asp Gly Thr Lys Gly Glu Lys Gly Glu Pro Gly
             30                  35                  40 caa ggg ctc aga ggc tta cag ggc ccc cct gga aag ttg ggg cct cca         302
Gln Gly Leu Arg Gly Leu Gln Gly Pro Pro Gly Lys Leu Gly Pro Pro
         45                  50                  55 gga aat cca ggg cct tct ggg tca cca gga cca aag ggc caa aaa gga         350
Gly Asn Pro Gly Pro Ser Gly Ser Pro Gly Pro Lys Gly Gln Lys Gly
 60                  65                  70                  75 gac cct gga aaa agt ccg gat ggt gat agt ctg gct gcc tca gaa           398
Asp Pro Gly Lys Ser Pro Asp Gly Asp Ser Leu Ala Ala Ser Glu
                 80                  85                  90
```

| | |
|---|---|
| aga aaa gct ctg caa aca gaa atg gca cgt atc aaa aag tgg ctg acc<br>Arg Lys Ala Leu Gln Thr Glu Met Ala Arg Ile Lys Lys Trp Leu Thr<br>         95                    100                   105 | 446 |
| ttc tct ctg ggc aaa caa gtt ggg aac aag ttc ttc ctg acc aat ggt<br>Phe Ser Leu Gly Lys Gln Val Gly Asn Lys Phe Phe Leu Thr Asn Gly<br>     110                    115                    120 | 494 |
| gaa ata atg acc ttt gaa aaa gtg aag gcc ttg tgt gtc aag ttc cag<br>Glu Ile Met Thr Phe Glu Lys Val Lys Ala Leu Cys Val Lys Phe Gln<br>125                    130                    135 | 542 |
| gcc tct gtg gcc acc ccc agg aat gct gca gag aat gga gcc att cag<br>Ala Ser Val Ala Thr Pro Arg Asn Ala Ala Glu Asn Gly Ala Ile Gln<br>140                    145                    150                   155 | 590 |
| aat ctc atc aag gag gaa gcc ttc ctg ggc atc act gat gag aag aca<br>Asn Leu Ile Lys Glu Glu Ala Phe Leu Gly Ile Thr Asp Glu Lys Thr<br>                      160                    165                    170 | 638 |
| gaa ggg cag ttt gtg gat ctg aca gga aat aga ctg acc tac aca aac<br>Glu Gly Gln Phe Val Asp Leu Thr Gly Asn Arg Leu Thr Tyr Thr Asn<br>     175                    180                    185 | 686 |
| tgg aac gag ggt gaa ccc aac aat gct ggt tct gat gaa gat tgt gta<br>Trp Asn Glu Gly Glu Pro Asn Asn Ala Gly Ser Asp Glu Asp Cys Val<br>          190                    195                    200 | 734 |
| ttg cta ctg aaa aat ggc cag tgg aat gac gtc ccc tgc tcc acc tcc<br>Leu Leu Leu Lys Asn Gly Gln Trp Asn Asp Val Pro Cys Ser Thr Ser<br>205                    210                    215 | 782 |
| cat ctg gcc gtc tgt gag ttc cct atc tgaagggtca tatcactcag<br>His Leu Ala Val Cys Glu Phe Pro Ile<br>220                    225 | 829 |
| gccctccttg tcttttact gcaacccaca ggcccacagt atgcttgaaa agataaatta | 889 |
| tatcaatttc ctcatatcca gtattgttcc ttttgtgggc aatcactaaa aatgatcact | 949 |
| aacagcacca acaaagcaat aatagtagta gtagtagtta gcagcagcag tagtagtcat | 1009 |
| gctaattata taatattttt aatatatact atgaggccct atcttttgca tcctacatta | 1069 |
| attatctagt ttaattaatc tgtaatgctt tcgatagtgt taacttgctg cagtatgaaa | 1129 |
| ataagacgga tttatttttc catttacaac aaacacctgt gctctgttga gccttccttt | 1189 |
| ctgtttgggt agagggctcc cctaatgaca tcaccacagt ttaataccac agcttttac | 1249 |
| caagtttcag gtattaagaa atctatttt gtaactttct ctatgaactc tgttttcttt | 1309 |
| ctaatgagat attaaaccat gtaaagaaca taaataacaa atctcaagca aacagcttca | 1369 |
| caaattctca cacacataca tacctatata ctcactttct agattaagat atgggacatt | 1429 |
| tttgactccc tagaagcccc gttataactc ctcctagtac taactcctag gaaaatacta | 1489 |
| ttctgacctc catgactgca cagtaatttc gtctgtttat aaacattgta tagttggaat | 1549 |
| catattgtgt gtaatgttgt atgtcttgct tactcagaat taagtctgtg agattcattc | 1609 |
| atgtcatgtg tacaaaagtt tcatccttt cattgccatg tagggttccc ttatattaat | 1669 |
| attcctcagt tcatccattc tattgttaat aggcacttaa gtggcttcca attttggcc | 1729 |
| atgaggaaga gaacccacga acattcctgg acttgtcttt tggtggacat ggtgcactaa | 1789 |
| tttcactacc tatccaggag tggaactggt agaggatgag gaaagcatgt attcagcttt | 1849 |
| agtagatatt accagttttc ctaagtgatt gtatgaattt atgctcctac cggcaatgtg | 1909 |
| tggcagtcct agatgctcta tgtgcttgta aaaagtcaat gttttcagtt ctcttgattt | 1969 |
| tcattattcc tgtggatgta aagtgatatt tccccatggt tttaatctgt atttccccaa | 2029 |
| catgtaataa ggttgaacac tttttatat gcttattggg cacttgggta tcttcttctg | 2089 |
| tgaagtaccc gttcacattt ttgtattttg tttaaattag ttagccaata tttttcttac | 2149 |

-continued

```
tgatttttaa gttatttta cattctgaat atgtcctttt taatgtgtat tacaaatatt    2209
ttgctagttt ttgacttgct cctaatgttg aattttgatg aacaaaattt cctaattttg    2269
agaaagtctt atttattcat atttctttc aaaattagtg cttttgtgt catgtttaag    2329 aaattttgc ccatcccaaa atcataagat attttcatg attttgaaac catgaagaga    2389
tttttcatga ttttgaaatc atgaagatat ttttccattt ttttctaata gttttattaa    2449
taaacattct atctattcct ggtagaatag atatccactg gagacagcac tatgtaggaa    2509
agaccatttt tcctccactg aactagggtg gtgcatttt gtaagttagg taactgtatg    2569
tgtgtgtgtc tgtttctggg ctgtctattc tagtctattt gttgatgctt gtgtcaaaca    2629
gtacactatc ttaattattg tacatttata gttgtaactg tagtccagct ttgttcttct    2689
tcaagtcaag atttccatat aaatattaga aacagtttct caatttctac aaaatcctga    2749
tgaggtttct actgggacca cattgagtct atcaatcaac ttatgcagaa ctggcaactt    2809
actactgaat ctcaatcaa tgttcatcat gtatcgcttc atttaactag gatttctcta    2869
acttaattgc tatgttttga gattttagt ttaaaaacct tgtatatctt gttttggtgg    2929
ttttagtgat tttaataata tattttaaat atttttctt ttctattgtt gtacacagaa    2989
atacagttaa gttttgtgtg tagtcttacg atgtttagta acctcaataa gtttatttct    3049
taaatctagt aatttgtaga ttcctctgga ttttgtatat gcatagtcat gtaagctgaa    3109
aatatggcaa tacttgcttc ttcccaattg ctttacctt ttctttacct tattgcactg    3169
gttagcaacc ccaatacaga gaccaccaga gcaggtatag actcctgaaa gacaatataa    3229
tgaagtgctc cagtcaggcc tatctaaact ggattcacag ctctgtcact taattgctac    3289
atgatctaga gccagttact ttgtgtttca gccatgtatt tgcagctgag agaaaataat    3349
cattcttatt tcatgaaaat tgtggggatg atgaaataag ttaacacctt taaagtgtgt    3409
agtaaagtat caggatacta tatttaggt cttaatacac acagttatgc cgctagatac    3469 atgctttta atgagataat gtgatattat acataacaca tatcgatttt taaaaattaa    3529
atcaaccttg ctttgatgga ataaactcca tttagtcaca aaaaaaaaaa aaaaaaaaa    3589 aaaaaaaaaa aaaaaa    3605
```

<210> SEQ ID NO 2
<211> LENGTH: 747
<212> TYPE: DNA
<213> ORGANISM: Homo sapiens

<400> SEQUENCE: 2

```
atgtccctgt ttccatcact ccctctcctt ctcctgagta tggtggcagc gtcttactca     60
gaaactgtga cctgtgagga tgcccaaaag acctgccctg cagtgattgc ctgtagctct    120
ccaggcatca acggcttccc aggcaaagat gggcgtgatg caccaaggg agaaaagggg    180 gaaccaggcc aagggctcag aggcttacag ggccccctg gaaagttggg gcctccagga    240
aatccagggc cttctgggtc accaggacca aggccaaa aaggagaccc tggaaaaagt    300
ccggatggtg atagtagcct ggctgcctca gaaagaaaag ctctgcaaac agaaatggca    360
cgtatcaaaa agtggctgac cttctctctg ggcaaacaag ttgggaacaa gttcttcctg    420
accaatggta aaataatgac cttgaaaaa gtgaaggcct tgtgtgtcaa gttccaggcc    480
tctgtggcca ccccaggaa tgctgcagag aatggagcca ttcagaatct catcaaggag    540
gaagccttcc tgggcatcac tgatgagaag acagaagggc agtttgtgga tctgacagga    600
aatagactga cctacacaaa ctggaacgag ggtgaaccca acaatgctgg ttctgatgaa    660
```

```
gattgtgtat tgctactgaa aaatggccag tggaatgacg tcccctgctc cacctcccat      720
ctggccgtct gtgagttccc tatctga                                         747
```

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: sense DNA

<400> SEQUENCE: 3

```
tatgccgcgg aatcgatgat taccgtacgg aattcgggcc c                         41
```

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: antisense
      DNA

<400> SEQUENCE: 4

```
acggcgcctt agctactaat ggcatgcctt aagcccggg                            39
```

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: sense DNA

<400> SEQUENCE: 5

```
agcttccgcg gctgcaggga tccatcgat                                       29
```

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: antisense
      DNA

<400> SEQUENCE: 6

```
aggcgccgac gtccctaggt agctattaa                                       29
```

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: 5' sense
      primer (PS1)

<400> SEQUENCE: 7

```
ccccgcggga attctgtgga atgtgtgtca gttaggg                              37
```

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: 3'
      antisense primer (PS2)

<400> SEQUENCE: 8

```
ccctgcagct ttttgcaaaa gcctaggcct cc                                   32
```

```
<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: 5' sense
      primer (PS3)

<400> SEQUENCE: 9
ccccgcggtg tggaatgtgt gtcagttagg g                          31

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: sense DNA

<400> SEQUENCE: 10
aattgggccc atcgat                                           16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: antisense
      DNA

<400> SEQUENCE: 11
cccgggtagc tattaa                                           16

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: 5' sense
      primer (PD1)

<400> SEQUENCE: 12
ggctgcagtc cctcatgctt cgaccattga actgcatcgt c               41

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: 3'
      antisense primer (PD2)

<400> SEQUENCE: 13
atagatctaa agccagcaaa agtcccatgg tc                         32

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:  5' sense
      primer (PN1)

<400> SEQUENCE: 14
ggctgcagct tcacgctgcc gcaagcac                              28
```

```
<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: 3'
      antisense primer (PN2)

<400> SEQUENCE: 15 gggatccgg ggtgggcgaa gaactccag                                    29

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: antisense
      primer

<400> SEQUENCE: 16
atcttgttca agcatgcgaa acgatcct                                    28

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: sense DNA

<400> SEQUENCE: 17
agcttgatat catcgatgcg gccgcggtac cagatctcgt acgtctagag             50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: antisense
      primer

<400> SEQUENCE: 18
actatagtag ctacgccggc gccatggtct agagcatgca gatctcttaa             50

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: 5' sense
      primer (PC1)

<400> SEQUENCE: 19
ccgattactt accgccatgt tgacattgat tattgactag ttattaa                47

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: 3'
      antisense primer (PC2)

<400> SEQUENCE: 20
ccatcgatcg gttcactaaa cgagctctgc ttatatagac ctccc                  45
```

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence:  5' sense
      primer (PB11)

<400> SEQUENCE: 21
cctctagact gtgccttcta gttgccagcc at                                    32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: 3'
      antisense primer (PB12)

<400> SEQUENCE: 22
ccagatctgt acccatagag cccaccgcat cc                                    32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:  5' sense
      primer (PB21)

<400> SEQUENCE: 23
ttggatccct gtgccttcta gttgccagcc at                                    32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence:  3'
      antisense primer (PB22)

<400> SEQUENCE: 24
ttcgtacgga tcccatagag cccaccgcat cc                                    32

<210> SEQ ID NO 25
<211> LENGTH: 7635
<212> TYPE: DNA
<213> ORGANISM: Artificial Sequence
<220> FEATURE:
<223> OTHER INFORMATION: Description of Artificial Sequence:  plasmid
      pNOW1

<400> SEQUENCE: 25
gcgcgtttcg gtgatgacgg tgaaaacctc tgacacatgc agctcccgga gacggtcaca      60
gcttgtctgt aagcggatgc cgggagcaga caagcccgtc agggcgcgtc agcgggtgtt     120
ggcgggtgtc ggggctggct taactatgcg gcatcagagc agattgtact gagagtgcac     180
catatgccgc ggtgtggaat gtgtgtcagt tagggtgtgg aaagtcccca ggctccccag     240
caggcagaag tatgcaaagc atgcatctca attagtcagc aaccatagtc cgcccctaa     300 ctccgcccat cccgcccta actccgccca gttccgccca ttctccgccc catggctgac     360 taatttttt tatttatgca gaggccgagg cgcctctgag ctattccaga agtagtgagg     420 aggcttttt ggaggcctag gcttttgcaa aaagctgca gtgggcttac atggcgatag     480
ctagactggg cggttttatg gacagcaagc gaaccggaat tgccagctgg ggcgccctct     540

```
ggtaaggttg ggaagccctg caaagtaaac tggatggctt tcttgccgcc aaggatctga    600
tggcgcaggg gatcaagatc tgatcaagag acaggatgag gatcgtttcg catgattgaa    660
caagatggat tgcacgcagg ttctccggcc gcttgggtgg agaggctatt cggctatgac    720
tgggcacaac agacaatcgg ctgctctgat gccgccgtgt tccggctgtc agcgcagggg    780
cgcccggttc tttttgtcaa gaccgacctg tccggtgccc tgaatgaact gcaggacgag    840
gcagcgcggc tatcgtggct ggccacgacg gcgttcctt gcgcagctgt gctcgacgtt    900
gtcactgaag cgggaaggga ctggctgcta ttgggcgaag tgccggggca ggatctcctg    960
tcatctcacc ttgctcctgc cgagaaagta tccatcatgg ctgatgcaat gcggcggctg   1020
catacgcttg atccggctac ctgcccattc gaccaccaag cgaaacatcg catcgagcga   1080
gcacgtactc ggatggaagc cggtcttgtc gatcaggatg atctggacga agagcatcag   1140
gggctcgcgc cagccgaact gttcgccagg ctcaaggcgc gcatgcccga cggcgaggat   1200
ctcgtcgtga cccatggcga tgcctgcttg ccgaatatca tggtggaaaa tggccgcttt   1260
tctggattca tcgactgtgg ccggctgggt gtggcggacc gctatcagga catagcgttg   1320
gctacccgtg atattgctga agagcttggc ggcgaatggg ctgaccgctt cctcgtgctt   1380
tacggtatcg ccgctcccga ttcgcagcgc atcgccttct atcgccttct tgacgagttc   1440
ttctgagcgg gactctgggg ttcgaaatga ccgaccaagc gacgcccaac ctgccatcac   1500
gagatttcga ttccaccgcc gccttctatg aaaggttggg cttcggaatc gttttccggg   1560
acgccggctg gatgatcctc cagcgcggga tcacatgctg gattcttcgc ccacccctc    1620 gatccctcg cgagttggtt cagctgctgc ctgaggctgg acgacctcgc ggagttctac   1680
cggcagtgca aatccgtcgg catccaggaa accagcagcg gctatccgcg catccatgcc   1740
cccgaactgc aggagtgggg aggcacgatg gccgctttgg tcgacccgga cgggacgctc   1800
ctgcgcctga tacagaacga attgcttgca ggcatctcat gagtgtgtct cccgttttc    1860 cgcctgaggt cactgcgtgg atgggatccg tgacataatt ggacaaacta cctacagaga   1920
tttaaagctc taaggtaaat ataaaatttt aagtgtata atgtgttaaa ctactgattc    1980
taattgtttg tgtattttag attccaacct atggaactga tgaatgggag cagtggtgga   2040
atgcctttaa tgaggaaaac ctgttttgct cagaagaaat gccatctagt gatgatgagg   2100
ctactgctga ctctcaacat tctactcctc caaaaaagaa gagaaaggta gaagacccca   2160
aggactttcc ttcagaattg ctaagttttt tgagtcatgc tgtgtttagt aatagaactc   2220
ttgcttgctt tgctatttac accacaaagg aaaaagctgc actgctatac cagaaattat   2280
gaaatattct gtaacccttta taagtaggca taacagttat aatcataaca tactgttttt   2340
tcttactcca cacaggcata gagtgtctgc tattaataac tatgctcaaa aattgtgtac   2400
ctttagcttt ttaatttgta aaggggttaa taaggaatat ttgatgtata gtgccttgac   2460
tagagatcat aatcagccat accacatttg tagaggtttt acttgcttta aaaaacctcc   2520
cacacctccc cctgaacctg aaacataaaa tgaatgcaat tgttgttgtt aacttgttta   2580
ttgcagctta taatggttac aaataaagca atagcatcac aaatttcaca aataaagcat   2640
ttttttcact gcattctagt tgtggtttgt ccaaactcat caatgtatct tatcatgtct   2700
gggcccgata tccgatgtac gggccagata tacgcgttga cattgattat tgactagtta   2760
ttaatagtaa tcaattacgg ggtcattagt tcatagccca tatatggagt tccgcgttac   2820
ataacttacg gtaaatggcc cgcctggctg accgcccaac gacccccgcc cattgacgtc   2880
aataatgacg tatgttccca tagtaacgcc aatagggact ttccattgac gtcaatgggt   2940
```

```
ggactatttta cggtaaactg cccacttggc agtacatcaa gtgtatcata tgccaagtac    3000 gcccccctatt gacgtcaatg acggtaaatg gcccgcctgg cattatgccc agtacatgac    3060
cttatgggaa ctttcctact tggcagtaca tctacgtatt agtcatcgct attaccatgg    3120
tgatgcggtt ttggcagtac atcaatgggc gtggatagcg gtttgactca cggggatttc    3180
caagtctcca ccccattgac gtcaatggga gtttgttttg gcaccaaaat caacgggact    3240
ttccaaaatg tcgtaacaac tccgccccat tgacgcaaat gggcggtagg cgtgtacggt    3300
gggaggtcta tataagcaga gcatcgatgc ggccgcggta cctctagact gtgccttcta    3360
gttgccagcc atctgttgtt tggcccccccc tccccgtgc cttccttgac cctggaaggt    3420
gccactccca ctgtcctttc ctaataaaat gaggaaattg catcgcattg tctgagtagg    3480
tgtcattcta ttctgggggg tggggtgggg caggacagca aggggagga ttgggaagac    3540 aatagcaggc atgctgggga tgcggtgggc tctatggtct aggctgtgcc ttctagttgc    3600
cagccatctg ttgtttggcc cccctcccc gtgccttcc ttgaccctgg aaggtgccac    3660
tcccactgtc ctttcctaat aaaatgagga attgcatcg cattgtctga gtaggtgtca    3720
ttctattctg gggggtgggg tgggcagga cagcaagggg gaggattggg aagacaatag    3780
caggcatgct ggggatgcgg tgggctctat ggcgtacggg atgctagaga attctgtgga    3840
atgtgtgtca gttagggtgt ggaaagtccc caggctcccc agcaggcaga agtatgcaaa    3900
gcatgcatct caattagtca gcaaccatag tccgcccct aactccgccc atcccgcccc    3960
taactccgcc cagttccgcc cattctccgc cccatggctg actaatttt tttatttatg    4020 cagaggccga ggcgcctctg agctattcca gaagtagtga ggaggctttt ttggaggcct    4080
aggcttttgc aaaaaagctg cagtccctca tggttcgacc attgaactgc atcgtcgccg    4140
tgtcccaaaa tatggggatt ggcaagaacg gagacctacc ctggcctccg ctcaggaacg    4200
agttcaagta cttccaaaga atgaccacaa cctcttcagt ggaaggtaaa cagaatctgg    4260
tgattatggg taggaaaacc tggttctcca ttcctgagaa gaatcgacct ttaaaggaca    4320
gaattaatat agttctcagt agagaactca aagaaccacc acgaggagct catttcttg    4380 ccaaaagttt ggatgatgcc ttaagactta ttgaacaacc ggaattgtca agtaaagtag    4440
acatggtttg gatagtcgga ggcagttctg tttaccagga agccatgaat caaccaggcc    4500
acctcagact ctttgtgaca aggatcatgc aggaatttga aagtgacacg ttttttcccag    4560 aaattgattt ggggaaatat aaacttctcc cagaataccc aggcgtcctc tctgaggtcc    4620
aggaggaaaa aggcatcaag tataagtttg aagtctacga aagaaagac taacaggaag    4680 atgctttcaa gttctctgct cccctcctaa agctatgcat ttttataaga ccatgggact    4740
tttgctggct ttaagatccg tgacataatt ggacaaacta cctacagaga tttaaagctc    4800
taaggtaaat ataaaatttt taagtgtata atgtgttaaa ctactgattc taattgtttg    4860 tgtatttttag attccaacct atggaactga tgaatgggag cagtggtgga atgcctttaa    4920
tgaggaaaac ctgttttgct cagaagaaat gccatctagt gatgatgagg ctactgctga    4980
ctctcaacat tctactcctc caaaaaagaa gagaaaggta aagaccccca aggactttcc    5040
ttcagaattg ctaagttttt tgagtcatgc tgtgtttagt aatagaactc ttgcttgctt    5100
tgctatttac accacaaagg aaaaagctgc actgctatac cagaaattat gaaatattct    5160 gtaacctttta taagtaggca taacagttat aatcataaca tactgttttt tcttactcca    5220
cacaggcata gagtgtctgc tattaataac tatgctcaaa aattgtgtac ctttagcttt    5280
ttaatttgta aaggggttaa taaggaatat ttgatgtata gtgccttgac tagagatcat    5340
```

```
aatcagccat accacatttg tagaggtttt acttgcttta aaaaacctcc cacacctccc    5400
cctgaacctg aaacataaaa tgaatgcaat tgttgttgtt aacttgttta ttgcagctta    5460
taatggttac aaataaagca atagcatcac aaatttcaca aataaagcat tttttttcact   5520 gcattctagt tgtggtttgt ccaaactcat caatgtatct tatcatgtct gggcccctgc    5580
attaatgaat cggccaacgc gcggggagag gcggtttgcg tattgggcgc tcttccgctt    5640
cctcgctcac tgactcgctg cgctcggtcg ttcggctgcg gcgagcggta tcagctcact    5700
caaaggcggt aatacggtta tccacagaat caggggataa cgcaggaaag aacatgtgag    5760
caaaaggcca gcaaaggcc aggaaccgta aaaaggccgc gttgctggcg ttttttccata     5820 ggctccgccc ccctgacgag catcacaaaa atcgacgctc aagtcagagg tggcgaaacc    5880
cgacaggact ataaagatac caggcgtttc ccctggaag ctccctcgtg cgctctcctg     5940
ttccgaccct gccgcttacc ggatacctgt ccgcctttct ccttcggga agcgtggcgc    6000 tttctcaatg ctcacgctgt aggtatctca gttcggtgta ggtcgttcgc tccaagctgg    6060
gctgtgtgca cgaacccccc gttcagcccg accgctgcgc cttatccggt aactatcgtc    6120
ttgagtccaa cccggtaaga cacgacttat cgccactggc agcagccact ggtaacagga    6180
ttagcagagc gaggtatgta ggcggtgcta cagagttctt gaagtggtgg cctaactacg    6240
gctacactag aaggacagta tttggtatct gcgctctgct gaagccagtt accttcggaa    6300
aaagagttgg tagctcttga tccggcaaac aaaccaccgc tggtagcggt ggtttttttg    6360
tttgcaagca gcagattacg cgcagaaaaa aaggatctca agaagatcct ttgatctttt    6420
ctacggggtc tgacgctcag tggaacgaaa actcacgtta agggattttg gtcatgagat    6480
tatcaaaaag gatcttcacc tagatccttt taaattaaaa atgaagtttt aaatcaatct    6540
aaagtatata tgagtaaact tggtctgaca gttaccaatg cttaatcagt gaggcaccta    6600
tctcagcgat ctgtctattt cgttcatcca tagttgcctg actccccgtc gtgtagataa    6660
ctacgatacg ggagggctta ccatctggcc ccagtgctgc aatgataccg cgagacccac    6720
gctcaccggc tccagattta tcagcaataa accagccagc cggaagggcc gagcgcagaa    6780
gtggtcctgc aactttatcc gcctccatcc agtctattaa ttgttgccgg gaagctagag    6840
taagtagttc gccagttaat agtttgcgca acgttgttgc cattgctaca ggcatcgtgg    6900
tgtcacgctc gtcgtttggt atggcttcat tcagctccgg ttcccaacga tcaaggcgag    6960
ttacatgatc ccccatgttg tgcaaaaaag cggttagctc cttcggtcct ccgatcgttg    7020
tcagaagtaa gttggccgca gtgttatcac tcatggttat ggcagcactg cataattctc    7080
ttactgtcat gccatccgta agatgctttt ctgtgactgg tgagtactca accaagtcat    7140
tctgagaata gtgtatgcgg cgaccgagtt gctcttgccc ggcgtcaata cgggataata    7200
ccgcgccaca tagcagaact ttaaaagtgc tcatcattgg aaaacgttct cggggcgaa     7260 aactctcaag gatcttaccg ctgttgagat ccagttcgat gtaacccact cgtgcaccca    7320
actgatcttc agcatctttt actttcacca gcgtttctgg gtgagcaaaa acaggaaggc    7380
aaaatgccgc aaaaaaggga ataagggcga cacggaaatg ttgaatactc atactcttcc    7440
tttttcaata ttattgaagc atttatcagg gttattgtct catgagcgga tacatatttg    7500
aatgtattta gaaaaataaa caatagggg ttccgcgcac atttccccga aaagtgccac     7560
ctgacgtcta agaaaccatt attatcatga cattaaccta taaaaatagg cgtatcacga    7620
ggccctttcg tcctc                                                    7635
```

```
<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 26
aaggaaaaaa gcggccgcat gtccctgttt ccatcactc                               39

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 27
gctctagatc agatagggaa ctcacagac                                          29

<210> SEQ ID NO 28
<211> LENGTH: 248
<212> TYPE: PRT
<213> ORGANISM: Homo sapiens

<400> SEQUENCE: 28
```

Met Ser Leu Phe Pro Ser Leu Pro Leu Leu Leu Ser Met Val Ala
 1               5                  10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
            35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
            115                 120                 125

Ser Leu Gly Lys Gln Val Gly Asn Lys Phe Phe Leu Thr Asn Gly Glu
        130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

RECOMBINANT HUMAN MANNAN-BINDING PROTEINS AND PRODUCING METHOD OF THE SAME

This application is a divisional application of U.S. patent application Ser. No. 09/600,950, filed Sep. 8, 2000, now abandoned, which is a 35 USC §371 national stage application of International patent application No. PCT/JP98/03311, filed on Jul. 23, 1998, which claims priority to Japanese application Hei 10-11864, filed on Jan. 23, 1998.

BACKGROUND ART

Mannan-Binding Proteins (hereinafter simply referred to as "MBP" and sometimes called as Mannose-Binding Proteins, Mannose-Binding Lectin (MBL) or Mannan-Binding Lectin (MBL)), Conglutinin, Surfactant Protein A (SP-A) and Surfactant Protein D (SP-D), and each of them belongs to a group called as collectin.

With reference to FIG. 1. collectin comprises basic constituent unit having the four unique regions of (1) calcium ion ($Ca^{2+}$)-dependent carbohydrate recognition domain (CRD). (2) neck region, (3) collagen-like region and (4) N-terminal region containing cystein [Malhotra et al., *European Journal of Immunology*, Vol. 22, pp. 1437–1445 (1992)], then triple helix are formed by twisting three constituent units (three units) at each of their collagen-like region, and subunits are formed.

Such subunits may further constitute oligomer structure like trimer, tetramer or hexamer. Of the collectins, MBP is specifically binding to Mannose or N-Acetyl-Glucosamine and needs calcium (ion) for such binding, for example, form of MBP from the human serum is homopolymer having, as the constituent units, the subunits in the molecular weight of about 32,000 Da [Teizo Fujita, "Complement Activation and Lectin Pathway", *Rinsho-Meneki*, Vol. 29, No. 3, pp-405–410 (1997)].

In vertebrates, mechanisms involving specific antibody reaction and immune response through the cells are considered as a main host-defense system against inversion of the pathogenic bacteria. However, recently, non-specific immune response by these lectins seems that it may play an important role to neutralize and remove the various microorganisms and virus in the puerile subjects having the maternal transmigration antibody and the undeveloped specific defense system [Super et al., *Lancet*, Vol.II, pp. 1236–1239 (1989): Nobutaka Wakamiya, Yasuhiko Suzuki, "Anti-Viral activity by Collectin" *Rinsho-Meneki*, Vol.29, No. 4, pp.508–513 (1997)].

Then, regarding the role of these lectins on biological defense in host organism, it is reported that infection will be easily spread by, for example, the reduction of MBP concentration in blood due to the genetic mutation of MBP gene [Sumiya et al., *Lancet*, Vol.337, pp.1569–1570 (1991)].

The present inventor once reported that the conglutinin and MBP inhibit infection and hemagulutination inhibition activities of H1 and H3 Type Influenza A Viruses [Wakamiya et al., *Glycoconjugate Journal*, Vol.8, p.235 (1991); Wakamiya et al., *Biochem. Biophys. Res. Comm.*, Vol.187, pp. 1270–1278 (1992)].

In particular, with respect to the human MBP (hereinafter simply referred to as "hMBP"), many aspects including their structure and their physiological functions (activities) have recently been Investigated eagerly. For example, Ezekowitz et al., reported the analysis results on the hMBP structure as their structure and their gene [Epstein et al., "The collectins in innate immunity", *Current Opinion in Immunology*, Vol.8, pp.29–35, (1996); Japanese Patent Translation Publication No. 2-504581].

On the other hand, as an aspect on biological-function of hMBP, hMBP have been considered that it involves with basal immunity like (i) anti-microbial activities, (ii) opsonin activities, (iii) complement activation [Kazuhide Uemura, et al., "Correlation between Structure and Function of Calcium Dependence Animal Lectin on Host Defence", *Jikken-Igaku*, Vol. 13, No. 18 (1995)]. With respect to an clinical application, in view of the findings obtained through analysis on deficit of MBP in blood, it had also been reported that cause of such deficit is gene mutation in collagen-like structure and, thereby, amino acids mutation, and, accordingly, both stabilities of MBP itself and MBP concentration in blood were reduced [Sumiya et al., "Mannose-binding protein, genetic variants and the risk of infection", *Q.J Med.*, No. 89, pp.723–726 (1996); Thomas et al., "Mutation of gene for mannose-binding protein associated with chronic hepatitis B viral infection", *The Lancet*, Vol.348, pp.1417–1419 (1996); Ezekowitz, "Mannose-binding protein and susceptibility to chronic hepatitis B infection", *The Lancet*, Vol. 348, pp.1396–1397 (1996)].

Also, it had been reported that MBP concentration in blood is concerned with a Pathogenicity of hepatitis B viral and HIV infection. In contrast thereto, it has also been suggested that MBP may involve with lectin pathway through MBP, due to abnormalities on sugar chain of immunoglobulin, in the disorder like chronical rheumatoid arthritis [Malhotra et al., "Glycosylation changes of IgG associated with rheumatoid arthritis can activate complement via the mannose-binding Protein", *Nature Medicine*, Vol.1, pp.237–243 (1995)] or IgA nephrosis [Mitsuhiro Matsuda et al., "Involvement of Mannan Binding Protein with crisis and progression of IgA nephrosis", *Journal of Nephrology Association of Japan*, vol.39, No.3, p.235 (1997)].

Further, according to the recent studies, it had also been reported that, besides the susceptibility to HIV by hMBP, it may involve with latency prior to crisis of AIDS (Acquired Immuno Deficiency Syndrome). hMBP may therefore contribute to prolong the life of AIDS patients [Garred, et al., "Susceptibility to HIV infection and progression of AIDS in relation to variant alleles of mannose-binding lectin", *The Lancet*, Vol, 349, pp.236–240 (1997)].

Unfortunately, although utilities of hMBP as physiologically active medical materials (components) have been expected, since the source of which is depended on the animal serum like human or rabbit serum, continuous production thereof was quite difficult and the yield thereof was very small. Further, artificial large scale production system for hMBP by gene recombination techniques have not yet been established.

DISCLOSURE OF INVENTION

The present inventions have been established through the continuous research to realize large-scale production of the homogenous hMBP in view of the aforenoted problems in the prior art.

Namely, hMBP (rhMBP) to be obtained by the present invention includes the characteristic rhMBP of:

rhMBP which offers the specific peaks at the molecular weight of 1,000~1,300 kDa, preferably 1,150 kDa, when it is applied to 280 nm absorbance in Gel-Filtration Chromatography;

rhMBP which offers the specific peaks at the molecular weight of 200~400 kDa, preferably 300 kDa, when it is applied to 280 nm absorbance in Gel-Filtration Chromatography; and rhMBP which offers the specific peaks at the molecular weight of 1,000~1,300 kDa and 200~400 kDa when it is applied to 280 nm absorbance in Gel-Filtration Chromatography.

The Present invention may also includes rhMBP prepared according to the method comprising the steps of:
(1) constructing the expression vector pNOW1-hMBP by inserting into plasmid pNOW1 cDNA corresponding to 66 bp~812 bp of cDNA from natural Human Mannan-Binding Proteins (hereinafter simply referred to as native MBP);
(2) preparing transformants by introducing said expression vector pNOW1-hMBP into Chinese Hamster Ovar (CHO) cells which are lack of dihydrofolate reductase (dhfr⁻);
(3) obtaining neomycin resistance cells by culturing said transformants in a culture medium containing neomycin;
(4) obtaining methotrexate (MTX) resistance cells by culturing the selected neomycin resistance cells in a culture medium containing MTX; and
(5) collecting rhMBP from the selected MTX resistance cells.

Amino acids which constitute native hMBP had already been analyzed and been reported by Herman et al [Sastry et al., "The human mannose-binding protein gene. Exon structure reveals its evolutionary relationship to a human pulmonary surfactant gene and localization to chromosome 10", J. Exp. Med. 170(4),1175–1189 (1989)], a base sequence from its cDNA is set out in SEQ. ID. NO:1 and a part of amino acids corresponding to such base sequence is set out in SEQ. ID. NO: 28.

Then, the present inventor planned to establish the production system of rhMBP by excising the particular base sequences involving protein expression of rhMBP, namely, cDNA (SEQ. ID. NO:2) corresponding to 66 bp~812 bp of the base sequences which constitute native hMBP, and incorporating it into an expression system.

BRIEF DESCRIPTION OF DRAWINGS

FIG. 2 shows a preparation scheme of Vector pBBV.
FIG. 3 shows a preparation scheme of Plasmid pCV3.
FIG. 11 shows the structure of Plasmid pNOW1.

Figure 1:
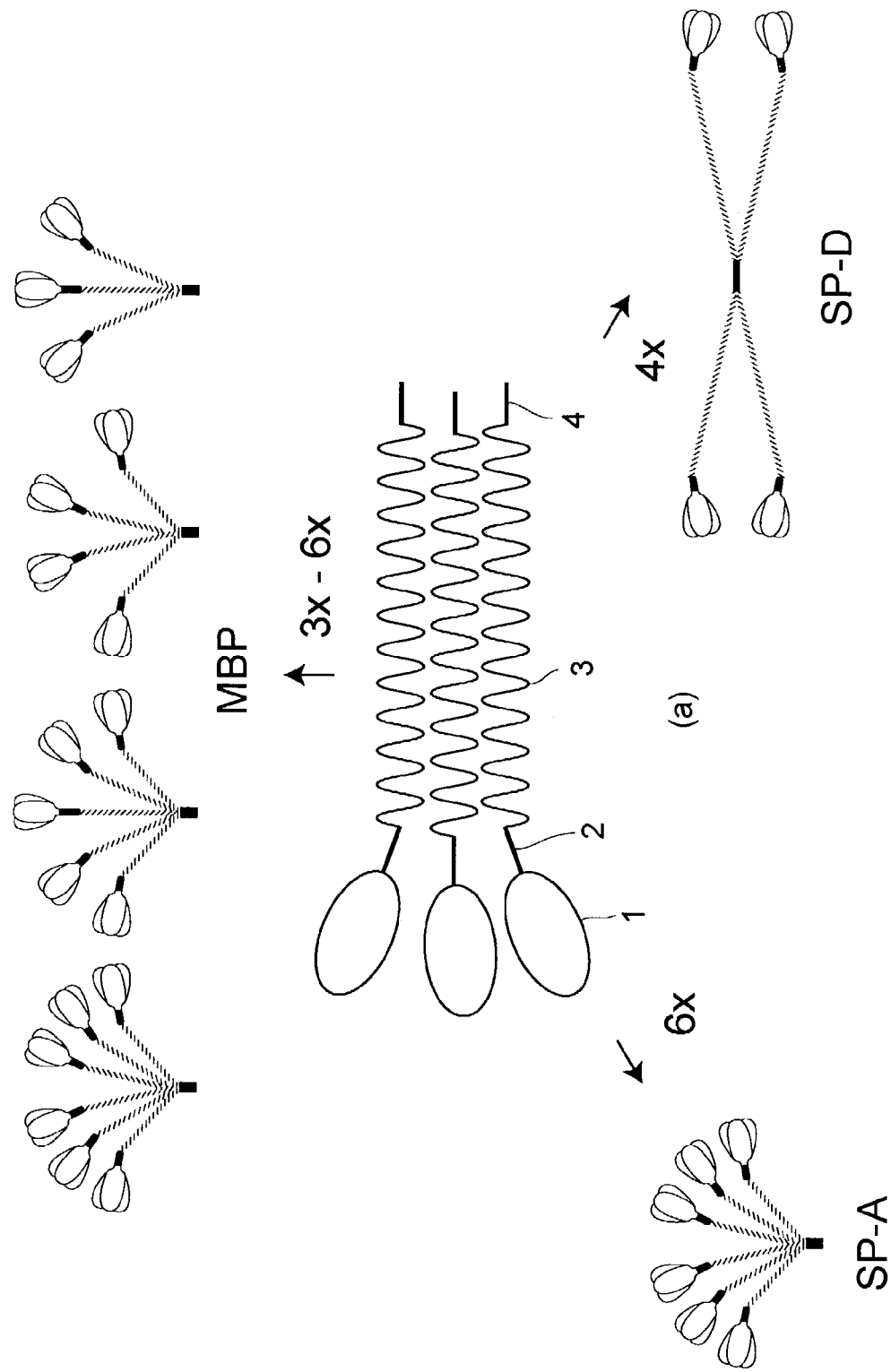
FIG. 1 shows a structure of collectins.

BEST MODE FOR CARRYING OUT INVENTION rhMBP of the present inventions will be explained in detail along with the following Examples, but, as a matter of course, scope of the present invention should not be limited based on the disclosure of the Examples.

Examples are consisting of; construction of plasmid pNOW1 (Example 1), construction of expression vector pNOW1-hMBP (Example 2), collection of the expression clone from neomycin (G418) resistance cells and MTX resistance cells (Example 3), structual analysis of rhMBP by PAGE analysis and Gel-Filtration Chromatography (Example 4), evaluation of glyco-binding activities on rhMBP and native hMBP (Example 5), evaluation of activities for hemagglutination inhibition (HI) (Example 6), evaluation of neutralization activities (Example 7), evaluation of activities for viral growth (infection spread) inhibition (Example 8), and evaluation of activities on rhMBP for activating complement (Example 9).

EXAMPLE 1

Preparation of Plasmid pNOW1

(1) Preparation of Back Bone Vector pBBV (FIG. 2)

Sense DNA having the base sequence set out in SEQ. ID. NO:3 and Anti-Sense DNA having the base sequence set out in SEQ. ID. NO:4 respectively were synthesized to additionally incorporate them as a linker (BBV linker) for multi-cloning sites into plasmid pUC18 (Takara Shuzo).

Sequence at site to be restricted by restriction enzymes in such linker is 3'-NdeI-SacII-ClaI-EcoRV-SPlI-EcoRI-ApaI-5' and 5'-end thereof is Blunt End. Coding region for lacZ were completely removed by digesting 1 ng (0.1 µl) of plasmid pUC18 with restriction enzymes NdeI and PvuII.

Into this solution, 100 pmole of sense DNA and anti-sense DNA respectively for BBV linker were added, then 2.0 µl of solution I attached to DNA ligation kit Ver.2 (Takara Shuzo) were further added, and these were reacted at 16° C. for 30 minutes, 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids inserted thereinto DNA of BBV linker were selected and designated them as vector pBBV.

(2) Preparation of Plasmid pCV3 (FIG. 3)

Multi-Cloning sites of plasmid pUC119 were removed. Then, sense DNA having the base sequence set out in SEQ. ID. NO:5 and Anti-Sense DNA having the base sequence set out in SEQ. ID. NO:6 respectively were synthesized to additionally incorporate them as a linker (CV3 linker) for multi-cloning sites into plasmid pUC119 (Takara Shuzo). Sequence at site to be restricted by restriction enzymes in such linker is 5'-HindIII-SacII-PstI-BamHI-ClaI-3' and 3'-end thereof is Blunt End. 1 ng (0.1 µl) of plasmid pUC119 was digested with the restriction enzymes HindIII and EcoRI.

Into the solution containing the plasmids so prepared, 100 pmole of sense DNA and anti-sense DNA respectively for CV3 linker were added, then 2.0 µl of solution I attached to DNA ligation kit Ver.2 (Takara Shuzo) were further added, and these were reacted at 16° C. for 30 minutes.

0.1 ml *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids inserted thereinto DNA of CV3 linker were selected and designated them as plasmid pVC3 (for cloning the SV40-related gene).

Figure 4:
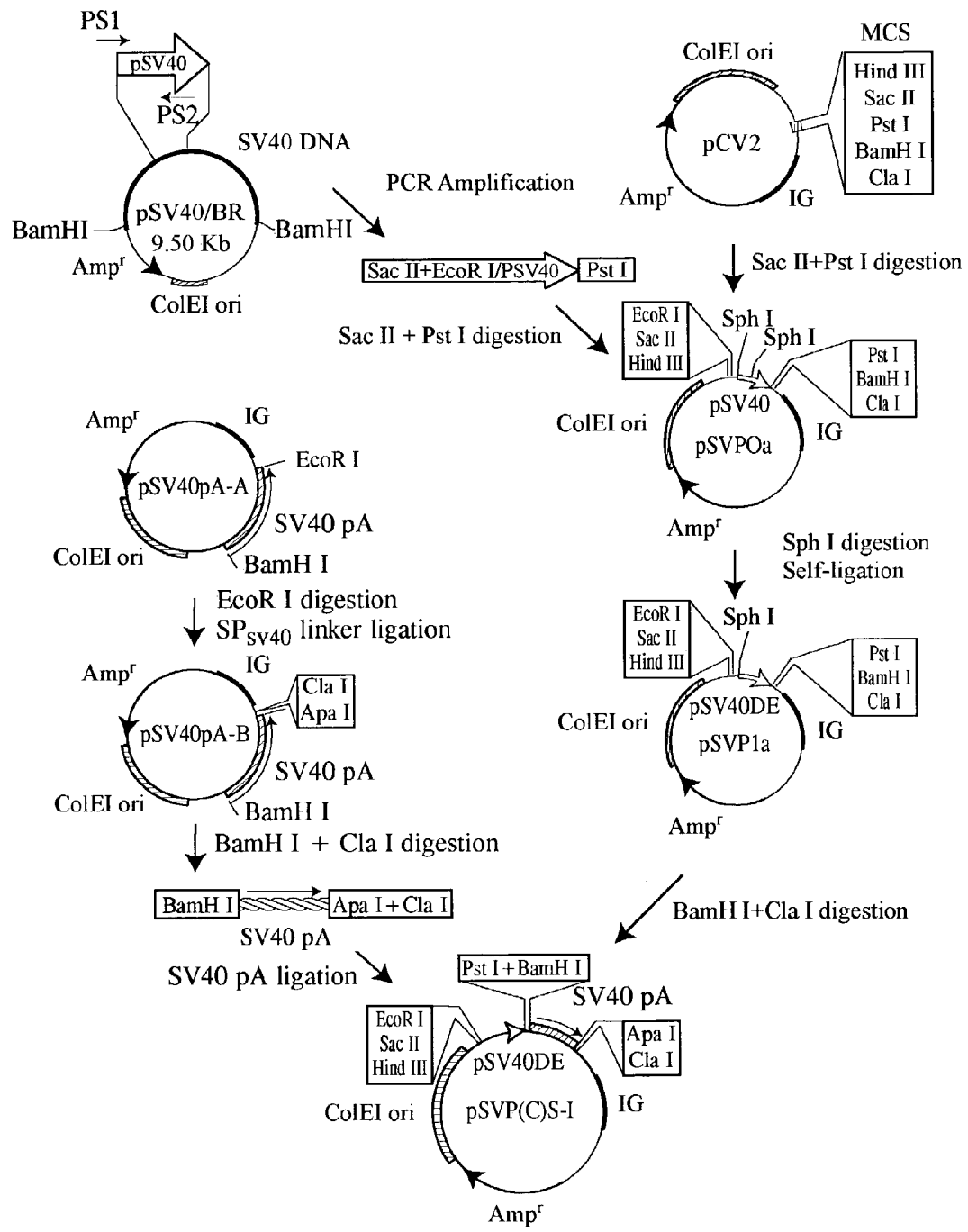
FIG. 4 shows a preparation scheme of Plasmid pSVP(D)S-1.

(3) Preparation of Plasmid pSVP(D)S-1 (FIG. 4)

(3-1) Preparation of Plasmid pSVP1a

5'-sense primer (PS1) having the base sequence set out in SEQ. ID. NO:7 and 3'-anti-sense primer (PS2) having the base sequence set out in SEQ. ID. NO:8 respectively were synthesized to excise SV40 initial promoter having SV40 0 ri from plasmid pSV40/BR (obtained from Hiroshima University) containing the whole DNA of SV40 virus ligated with BamHI on pBR322. 5'-end of PS1 primer have restriction site of SacII-EcoRI instead of the PvuII site in the original sequence. Then, 3'-end of PS2 primer have PstI site instead of the original HindIII site. To 1 ng (0.1 µl) of pSV40/BR genome (from pSV40/BR, obtained from Hiroshima University), 100 pmole of PS1 primer and PS2 primer respectively, 2.5U (0.5 µl) of Taq polymerase (Takara Shuzo), 20 µl of PCR Buffer (250 mM Tris-HCl (pH 8.3 at 25° C.), 375 mM KCl, 15 mM MgCl$_2$), 0.1 µl of 100 mM DTT, 0.5 µl of 10 mM dNTP (10 mM dATP, dCTP, dGTP, dTTP) and 0.25 µl of acetylated BSA(4 mg/ml) were added, then were adjusted with the sterilized water to make its final volume 100 µl.

One drop of the mineral oil (Sigma Chemical) was added to these mix solution, then PCR was Performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C.

Liquid phases were taken from this PCR reaction solution, and, to 10 µl of which, 2 µl of 10×H solution, 20U(1 µl) of the restriction enzyme SacII as well as 20U(1 µl) of the restriction enzyme PstI and 7 µl of the sterilized water were added and it was incubated at 37° C. for one hour. The reaction solution was then applied to an electrophoresis employing 0.8% agarose-gel at 50 mA for 30 minutes. Approximately 0.35 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet. Plasmid pCV3 were treated with SacII and PstI, then 5 µl of said DNA solution was added thereto, and 2.0 µl of solution I attached to DNA ligation kit Ver.2 (Takara Shuzo) were further added thereto, and these were incubated at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids inserted thereinto DNA of SV40 promoter were selected and designated them as pSVOa. Plasmid pSVP1a containing PSV40DE having SacII-EcoRI site at 5'-end thereof were further prepared by self-ligating such plasmids with the restriction enzyme SphI and removing its enhancer portion.

(3-2) Preparation of Plasmid pSVP1b

Plasmid pSVP1b containing SV40 Promoter PSV40DE for NEO gene cistron were prepared in accordance with the preparation scheme of Example 1 (3-1) except that 5'-sense primer (PS3) having the base sequence set out in SEQ. ID. NO:9 was synthesized instead of 5'-sense primer (PS1). P3 primer have SacII site only at 5'-end thereof (without EcoRI site).

(3-3) Preparation of SV40 polyA

Into 3'-end EcoRI site in SV40 polyA signal sequence of Plasmid PSV40PA-A (from pSV40/BR, obtained from Hiroshima University) having polyadenylation (herein referred to as "polyA") signal derived from SV40 virus genome, SPSV40 linker were ligated, thereby, EcoRI site was altered to ApaI-ClaI site. Firstly, as SPSV40 linker, sense DNA having the base sequence set out in SEQ. ID. NO:10 and anti-sense DNA having the base sequence set out in SEQ. ID. NO:11 respectively were synthesized.

1 ng (0.1 µl) of Plasmid PSV40pA-A was digested with the restriction enzyme EcoRI. Into the solution so prepared, 100 pmole of both sense DNA and anti-sense DNA for SPSV40 linker were added, then 2.0 µl of solution I attached to DNA ligation kit Ver.2 (Takara Shuzo) were further added thereto, and these were reacted at 16° C. for 30 minutes.

0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. After left it on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto DNA of SV40 polyA were selected and designated them as PSV40pA-B.

(3-4) Preparation of pSVP(D)S-1

To 1 ng (0.1 μl) of Plasmid pSV40pA-B, 20U (1 μl) of the restriction enzyme BamHI as well as 20U (1 μl) of the restriction enzyme ClaI and 7 μl of the sterilized water were added, and it was reacted at 37° C. for one hour. The reaction solution was then applied to an electrophoresis employing 0.8% agarose-gel at 50 mA for 30 minutes. Approximately 0.8 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution using pipet. Plasmid pSV1a were treated with BamHI and ClaI, then 5 μl of said DNA solution was added thereto at the ratio of 1 ng per 0.1 μl of the solution, and 2.0 μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRAT-AGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids additionally inserted thereinto DNA of SV40 polyA were selected and designated them as Plasmid pSVP(D)S-1.

Figure 5:
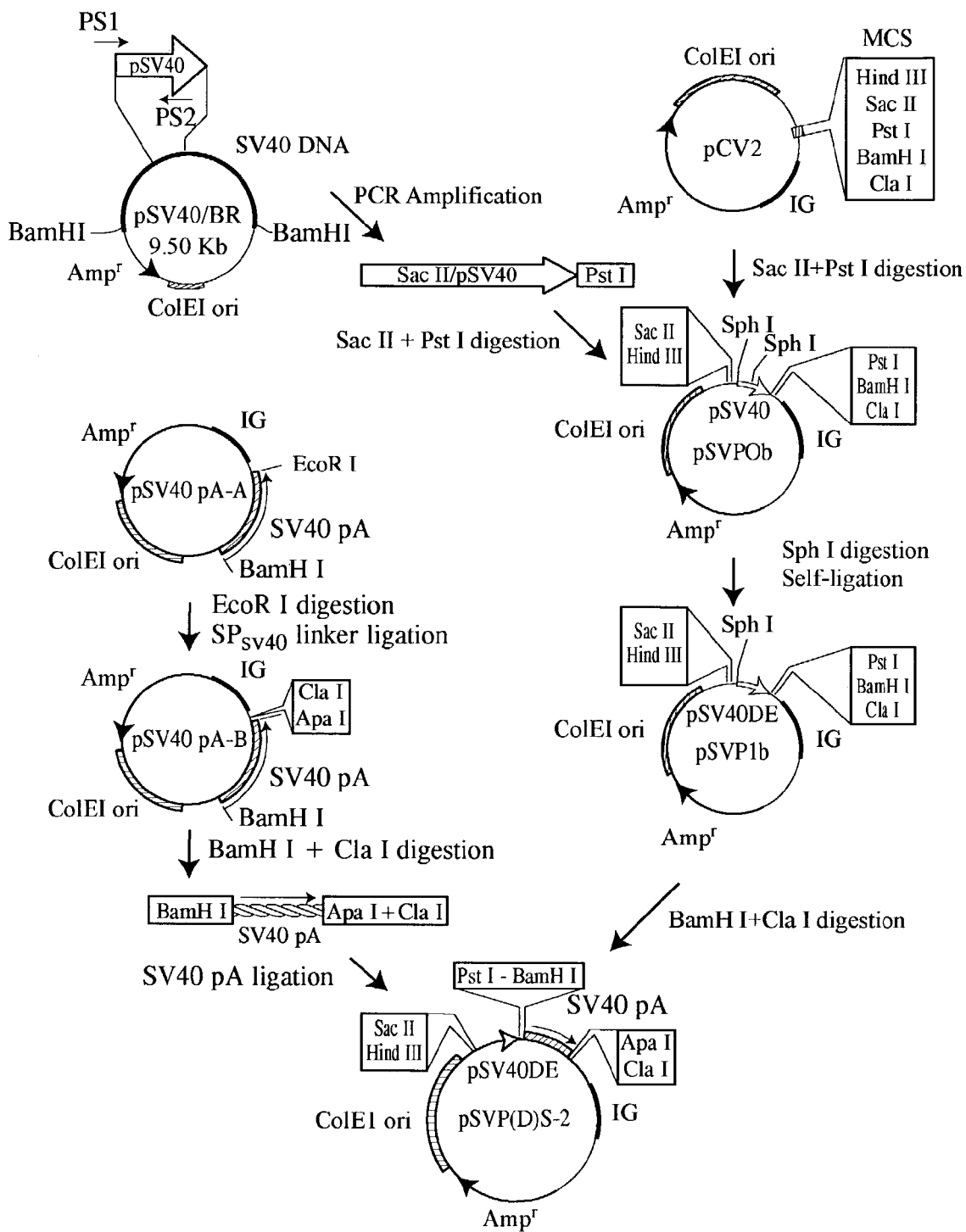
FIG. 5 shows a preparation scheme of Plasmid pSVP(D)S-2.

(4) Preparation of Plasmid pSVP(D)S-2 (FIG. 5)

Plasmid pSVP(D)S-2 containing SV40 Promoter for NEO gene cistron and SV40 polyA were prepared based on Plasmid pSVP1b and DNA of SV40 polyA from PSV40pA-B in accordance with the preparation scheme of Example 1 (3) for Plasmid pSVP(D)S-1.

Figure 6:
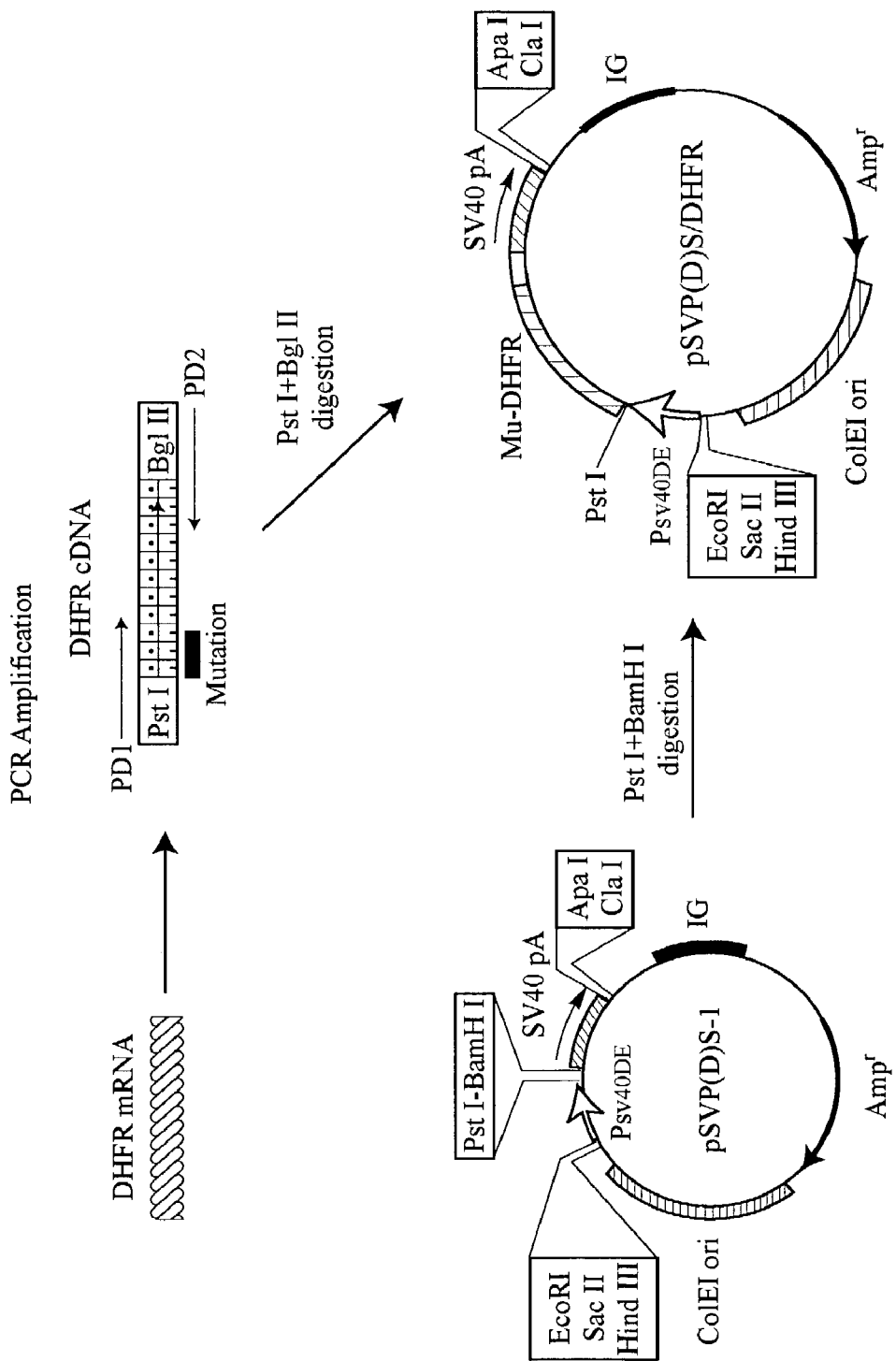
FIG. 6 shows a preparation scheme of Plasmid pSVP(D)S/DHFR.

(5) Preparation of Plasmid pSVP(D)S/DHFR (FIG. 6)

(5-1) Cloning on DHFR gene mRNA were isolated from $10^7$ cells of cultured mouse fibroblast strain 3T3 according to guanidine isothiocyanate method (Meth. Enzymol., 152, p.219, (1987)). Firstly, cells were floated in the flask, then the cells were re-floated in the sterilized PBS and transferred them to the centrifugation tubes. Under the temperature of 0° C. or below, the tubes were centrifuged at 450×g for 10 minutes, and the supernatant was then discarded. To the mix solution consisting of 6M GTG-CsCl, 10 mM sodium citrate, 0.1 ml β-mercaptoethanol and 0.5% sarcosil, cells so produced were added, then it was suspended and dissolved therein, and RNA were fragmented by passing it through 18-gauge needle. 2.5 ml of the solution so prepared were overlayered on 2.5 ml of the solution containing 5.7 M CsCl, and 0.1 M EDTA solution in an ultra-centrifugation tube. This was centrifuged at 35,000 rpm for 8 hours with an ultra-centrifugation, then the supernatant was discarded carefully, and RNA fractions deposited in the bottom of the tube were extracted with saturated phenol and were dissolved in the sterilized water.

Next, ethanol was added to the deposits and RNA were deposited with centrifugation at 12,000 rpm. Then, the deposits were rinsed three times with ethanol and were air-dried. RNA so produced were re-suspended with 3 ml of RNase-free water. Concentration of mRNA sample so obtained were about 0.3 μg/μl determined by absorbance at 260 nm.

(5-2) Preparation of DHFR cDNA

5'-sense primer (PD1) having the base sequence set out in SEQ. ID. NO:12 and 3'-anti-sense primer (PD2) having the base sequence set out in SEQ. ID. NO:13 respectively were synthesized to amplify the gene of DHFR.

5'-end is a sequence artificially combined PstI site with the nonsense pyrimidine sequence of "TCCCTC", while 3'-end is a sequence extended from the termination codon to the BglII site which is about 85 b downstream therefrom. 10 μl of solution containing 2 μg whole RNA was used to synthesize cDNA. Into the sterilized RNase-free tubes, 20 μl of PCR Buffer (250 mM Tris-HCl (pH 8.3 at 25° C.), 375 mM KCl, 15 mM MgCl$_2$), 1.0 μl of 100 mM DTT, 0.5 μl of 10 mM dNTP (10 mM dATP, dCTP, dGTP, dTTP), 0.25 μl of acetylated BSA (4 mg/ml), 2.0 μg of oligo-dT-primer, 0.5 μl of PCR reverse transcriptase (200 units/μl) and 0.5 μl of RNase-free DEPC water were added. These were incubated at 37° C. for 60 minutes, and the reaction was terminated by heating it at 70° C. for 15 minutes, cDNA so produced were directly added to the reaction solution for PCR prepared previously. To this solution, 100 pmole of PD1 primer and PD2 primer respectively were added, then, 2.5U (0.5 μl) of Taq polymerase (Takara Shuzo), 20 μl of PCR Buffer (250 mM Tris-HCl (pH 8.3 at 25° C.), 375 mM KCl, 15 mM MgCl$_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, and were adjusted with the sterilized water to make its final volume 100 μl. One drop of the mineral oi (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20U (1 μl) of the restriction enzyme PstI as well as 20U (1 μl) of the restriction enzyme BglII and 7 μl of the sterilized water were added and it was reacted at 37° C. for one hour. The reaction solution was then applied to an electrophoresis employing 0.8% agarose-gel at 50 mA for 30 minutes. Approximately 0.65 kb band was detected by exposuring it to the ultraviolet rays of 360 nm wavelength and was excised therefrom. These agarose fragments were poured into 1.5 ml tubes, then the tubes were centrifuged at 15,000 rpm for 10 minutes, and DNA solution was obtained by separating the solution using pipet.

(5-3) Preparation of Plasmid pSVP(D)S/DHFR

Plasmid pSVP(D)S-1 was partially digested with the restriction enzymes PstI and BamHI (this treatment is due to the presence of one PstI site in SV40 polyA). 0.5 μl of DHFR DNA solution was added to 0.1 μl (1 ng DNA) of this solution, 5'-end thereof is bond with PstI, while 3'-end thereof is bond with the projected ends of BamHI and BglII. At this moment, 2.0 μl of solution I attached to DNA ligation kit Ver.2 (Takara Shuzo) were added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids additionally inserted thereinto DNA of DHFR as well as the restriction site for ApaI were selected and designated them as Plasmid pSVP(D)S/DHFR.

Figure 7:
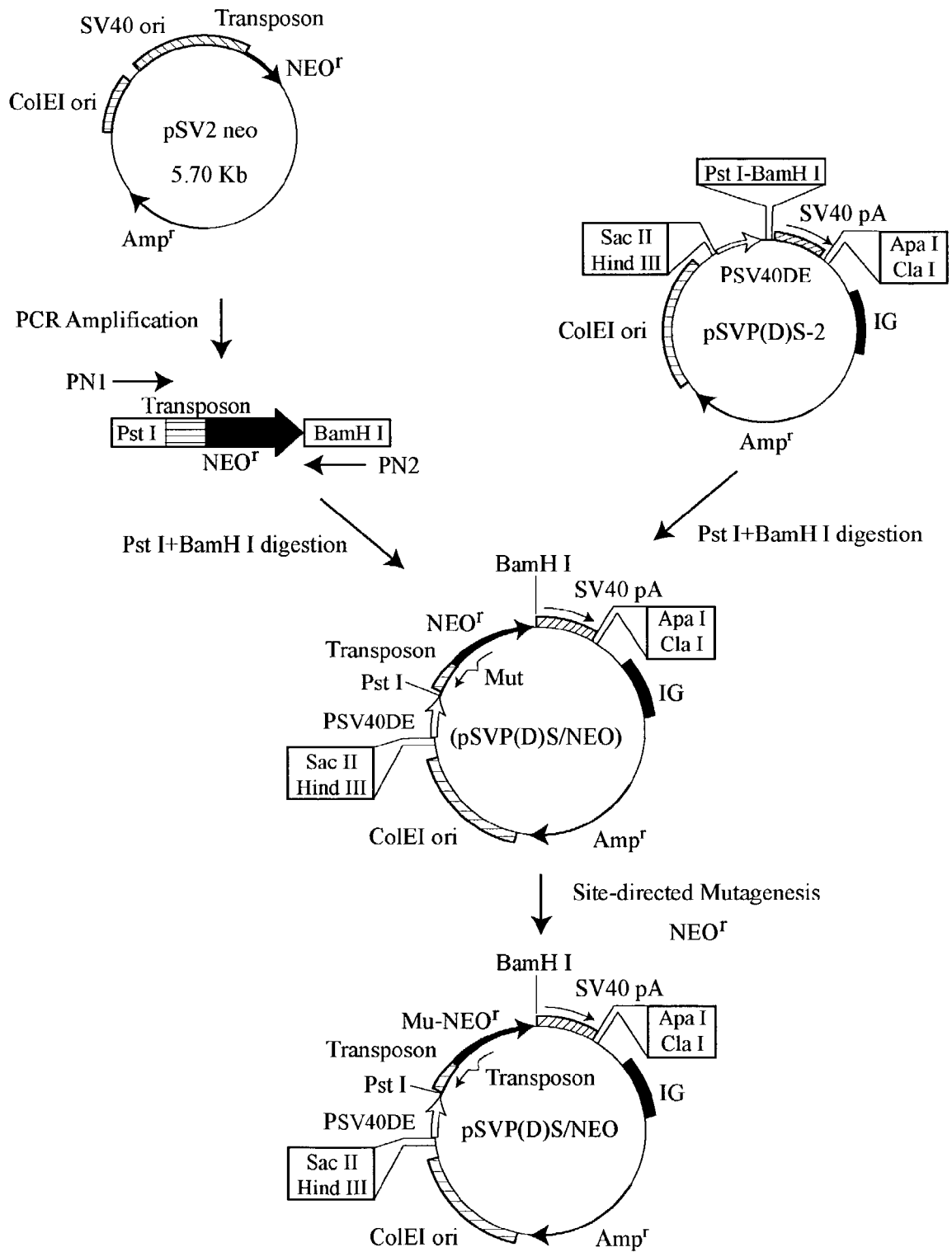
FIG. 7 shows a preparation scheme of Plasmid pSVP(D)S/NEO.

(6) Preparation of Plasmid pSVP(D)S/NEO (FIG. 7)

For Neomycin Phosphotransferase Gene (NEO gene) region, a sequence conjugated NEO gene translation region with the transposon sequence of 354 bases at 5'-upstream was used. This sequence is from Tn5 and is contained in pSV2-neo (J. Mol. Appl. Genet., p.1327 (1982)), therefore, this was prepared by excising it from pSV2-neo. Firstly, 5'-sense primer (PN1) having the base sequence set out in SEQ. ID. NO: 14 and 3'-anti-sense primer (PN2) having the base sequence set out in SEQ. ID. NO:15 respectively were synthesized, 5'-end of PN1 primer have PstI site instead of HindIII site in the original sequence. Then, 3'-end of PN2 primer have BamHI site instead of SmaI site in the original sequence.

To 1 ng (0.1 μl) of pSV2-neo genome, 100 pmole of PN1 primer and PN2 primer respectively were added, then, 2.5U (0.5 μl) of Taq polymerase (Takara Shuzo), 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, and were adjusted with the sterilized water to make its final volume 100 μl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20U (1 μl) of the restriction enzyme PstII as well as 20U (1 μl) of the restriction enzyme BamHI and 7 μl of the sterilized water were added and it was reacted at 37° C. for one hour. The reaction solution was then applied to an electrophoresis employing 0.8% agarose-gel at 50 mA for 30 minutes. Approximately 1.3 kb band was detected by exposuring it to the ultraviolet rays of 360 nm wavelength and was excised therefrom.

These agarose fragments were poured into 1.5 ml tubes, then the tubes were centrifuged at 15,000 rpm for 10 minutes, and DNA solution was obtained by separating the solution so produced with a pipet.

Plasmid pSVP(D)S-2 was partially digested with the restriction enzymes PstI and BamHI (this treatment is due to the presence of one PstI site in SV40 polyA), 0.5 μl of DNA solution of NEO gene were added to 0.1 μl (1 ng DNA) of this solution, thereby, PstI site and BamHI site were ligated.

With respect to this reaction, 2.0 μl of solution I attached to DNA ligation kit Ver.2 (Takara Shuzo) were added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto DNA of transposon sequence containing NEO gene were selected with regard to G418 resistance.

Further, anti-sense primer for introducing mutation which have the base sequence set out in SEQ. ID. NO:16 was synthesized to alter the base of "A" to "C" wherein the base "A" is immediately next to the initiation codon "ATG" in NEO gene translation region. 100 pmole of this anti-sense primer was added to 1 ng (1 μl) of pSVP(D)S/NEO genome, and was site-directed mutated by PCR in vitro Mutagenesis Kit (Takara Shuzo).

2.5U (0.5 μl) of Taq polymerase (Takara Shuzo), 20 μl of PCR Buffer (250 mM Tris-HCl (pH 8.3 at 25° C.), 375 mM KCl, 15 mM $MgCl_2$), 1.0 μl of 100 mM DTT, 0.5 μl of 10 mM dNTP (10 mM dATP. dCTP, dGTP, dTTP) and 0.25 μl of acetylated BSA (4 mg/ml) were added, and were adjusted with the sterilized water to make its final volume 100 μl. One drop of the mineral oil (Sigma Chemical) was added to these mix solution, then PCR was performed according to the following condition.

Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Plasmid vector so produced was designated as Plasmid pSVP(D)S/NEO.

(7) Preparation of Plasmid pEXP-BL2

Figure 8:
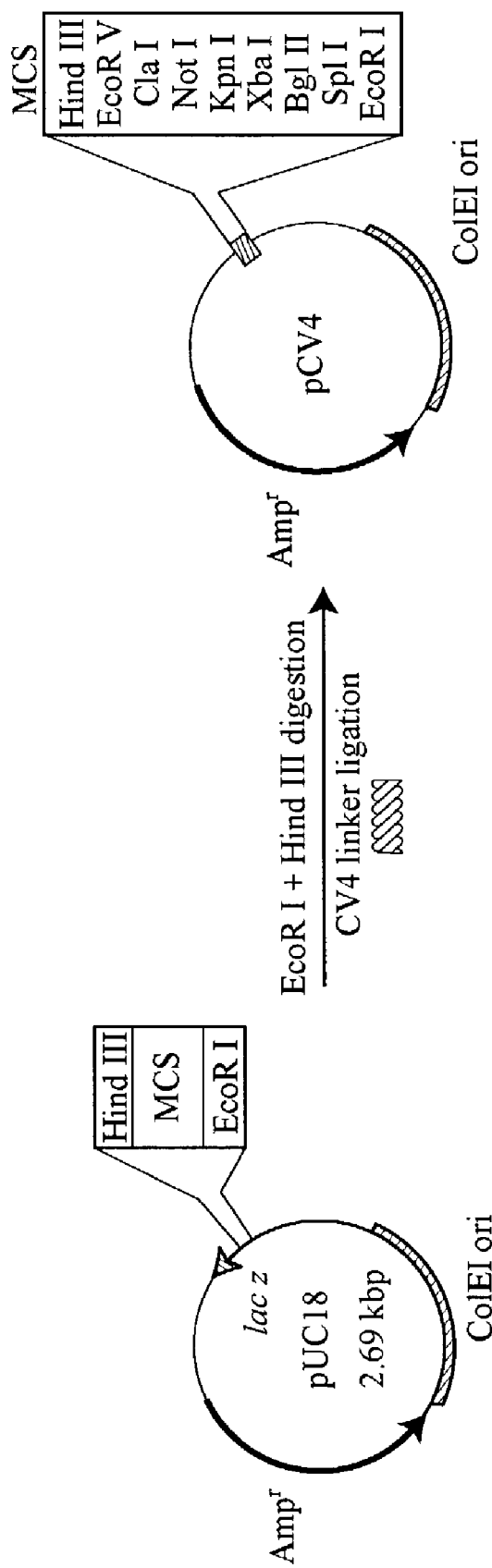
FIG. 8 shows a preparation scheme of Plasmid pCV4.

(7-1) Preparation of Plasmid pCV4 (FIG. 8)

Sense DNA having the base sequence set out in SEQ. ID. NO:17 and anti-sense DNA having the base sequence set out in SEQ. ID. NO:18 respectively were synthesized as a linker (CV4 linker) for Multi-Cloning Site to remove the Multi-Cloning site of Plasmid pUC18 (Takara Shuzo) and additionally incorporate thereinto Multi-Cloning Site (MCS) related gene.

Sequences at a site to be restricted by the restriction enzymes in this linker is 3'-HindIII-EcoRV-ClaI-NotI-KpnI-XbaI-BalII-SplI-EcoRI-5', 1 ng (0.1 μl) of Plasmid pUC18 was treated with the restriction enzymes of HindIII and EcoRI.

Into the solution containing the plasmids so produced, 100 pmole of sense DNA and anti-sense DNA respectively for CV4 linker were added, then 2.0 μl of solution I attached to DNA ligation kit Ver.2 (Takara Shuzo) were further added, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 μg/ml ampicillin respectively. After the overnight cultured at 37° C., of the plasmids collected from the colonies so produced, plasmids inserted thereinto DNA of CV4 linker were selected and designated them as vector pCV4.

Figure 9:
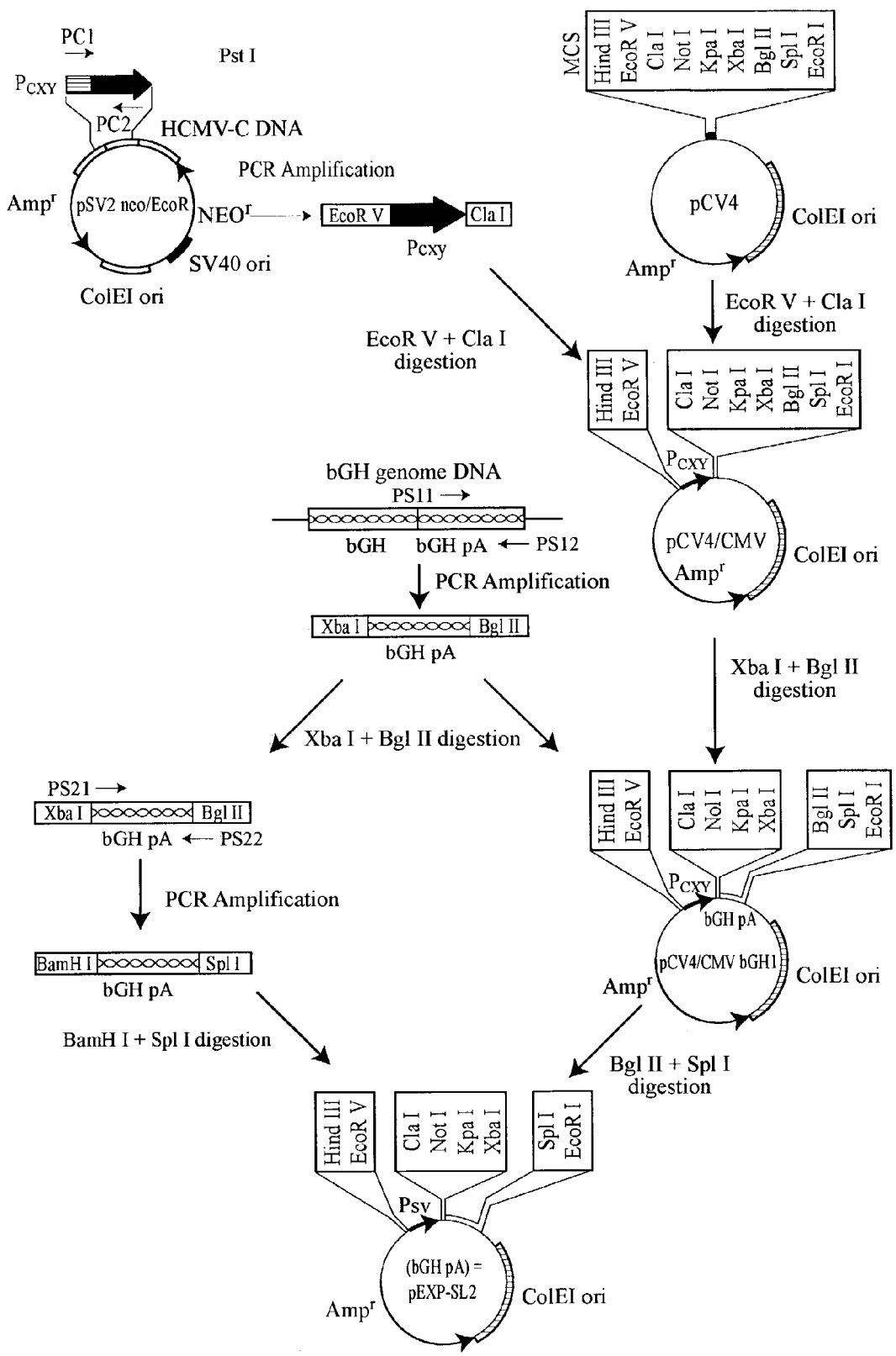
FIG. 9 shows a preparation scheme of Vector pEXP-BL2.

(7-2) Preparation of $P_{CMV}$ (FIG. 9)

5'-sense primer (PC1) having the base sequence set out in SEQ. ID. NO:19 and 3'-anti-sense primer (PC2) having the base sequence set out in SEQ. ID. NO:20 respectively were synthesized to excise $P_{CMV}$ from plasmid pSV2-neo/EcoH (obtained from Tokai University) prepared by incorporating the approximately 6 kb sequence containing the promoter/enhancer region of hCMV MIE antigen into PSV-Neo. 5'-end of PC1 primer have restriction site of EcoRV, while 3'-end of PC2 primer have ClaI site. To 1 ng (0.1 μl) of the plasmid pSV2-neo/EcoH genome, 100 pmole of PC1 primer and PC2 primer respectively, 2.5U (0.5 μl) of Taq polymerase (Takara Shuzo), 20 μl of PCR Buffer (250 mM Tris-HCl (pH 8.3 at 25° C.), 375 mM KCl, 15 mM MgCl$_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, then were adjusted with the sterilized water to make its final volume 100 μl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20U(1 μl) of the restriction enzyme EcoRV as well as 20U(1 μl) of the restriction enzyme ClaI and 7 μl of the sterilized water were added and it was reacted at 37° C. for one hour.

The reaction solution was then applied to an electrophoresis employing 0.8% agarose-gel at 50 mA for 30 minutes. Approximately 0.6 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet.

(7-3) Insertion of $P_{CMV}$ into Plasmids 1 ng (0.1 μl) of Plasmid pCV4 were treated with the restriction enzymes of EcoRV and ClaI, then 0.5 μl of $P_{CMV}$ DNA solution was added, and it was ligated to between EcoRV site and ClaI site. Into this reaction, 2.0 μl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to Proceed the reaction followed by heat-shock at 42° C. for 60 seconds. It had been left on ice for 2 minutes, 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 μg/ml ampicillin respectively. After the overnight culture at 37° C., of the plasmids collected from the colonies so produced, plasmids inserted thereinto $P_{CMV}$ DNA were selected and designated them as pCV4/CMV.

(7-4) Isolation of DNA having bGH polyA

While cell tissues obtained from bovine liver were sliced on the dry ice, they were extracted with the buffer (150 mM NaCl, 10 mM Tris-HCl (pH 8.0), 10 mM EDTA, 0.1% SDS) containing Proteinase K solution adjusted its concentration to be 100 μg/ml and were mixed gently. After one hour incubation at 55° C. they were further incubated overnight at 37° C. Then, equivalent amount of the neutral phenol equilibrated with Tris were added thereto and they were mixed gently at the room temperature for 20 minutes.

After the centrifugation at 2,000×g under the room temperature for 10 minutes, the upper layer (5 ml) so separated was collected, then the collected layers were transferred to the fresh tubes, and they were centrifuged again under the same condition. Upper layer was collected again and was transferred to the fresh tubes, and they were re-centrifuged under the same condition. Upper layer thereof was collected again and was transferred to the fresh tubes, then, two times volume of 100% ethanol were overlayered thereon, and the buffer and ethanol were mixed with gentle agitation, DNA so produced were collected by rolling it with glass-stick then were air-dried, and 5 ml of TE solution was added thereto and it was dissolved at 4° C. overnight.

Concentration of DNA sample so obtained were about 0.5 μg/μl determined by absorbance at 260 nm.

(7-5) Insertion of bGH polyA into Plasmids

Two types of bGH polyA sequences, each of which have the different sites on the restriction enzymes, were prepared to doubly conjugate bGH polyA sequences. Firstly, two pairs of 5'-sense primer and 3'-anti-sense primer, namely, one pair of 5'-sense primer (PB11) having the base sequence set out in SEQ. ID. NO:21 and 3'-anti-sense primer (PB12) having the base sequence set out in SEQ. ID. NO:22, and the other pair of 5'-sense primer (PB21) having the base sequence set out in SEQ. ID. NO:23 and 3'-anti-sense primer (PB22) having the base sequence set out in SEQ. ID. NO:24 were synthesized.

bGH polyA sequences having at its both ends the desired sequences to be restricted by restriction enzymes were prepared from 100 ng of DNA sample so synthesized by using PCR template.

Firstly, to 100 ng (1 μl) of DNA sample, 100 pmole of sense primer PB11 and anti-sense primer PB12 respectively, 2.5U (0.5 μl) of Taq polymerase (Takara Shuzo), 20 μl of PCR Buffer (250 mM Tris-HCl (pH 8.3 at 25° C.), 375 mM KCl, 15 mM MgCl$_2$), 1.0 μl of 100 mM DTT, 0.5 μl of 10 mM dNTP (10 mM dATP, dCTP, dGTP, dTTP) and 0.25 μl of acetylated BSA (4 mg/ml) were added, then were adjusted with the sterilized water to make its final volume 100 μl. One drop of the mineral oil (Sigma Chemical) was added to these mix solution, then PCR was performed according to the following condition.

Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid phases were taken from this PCR reaction solution, and, to 10 μl of which, 2 μl of 10×H solution, 20U (1 μl) of the restriction enzyme XbaI as well as 20U (1 μl) of the restriction enzyme BglII and 7 μl of the sterilized water were added and it was reacted at 37° C. for one hour.

The reaction solution was then applied to an electrophoresis employing 0.8% agarose-gel at 50 mA for 30 minutes.

Approximately 0.23 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet.

Into 0.1 µl (1 ngDNA) of solution wherein Plasmid pCV4/CMV was treated with XbaI and BglII, 0.5 µl of DNA solution noted above were added, then 2.0 µl of solution I attached to DNA ligation kit Ver.2 (Takara Shuzo) were further added, and these were reacted at 16° C. for 30 minutes.

0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, 0.9 ml of SOC medium (Toyobo) was added thereto and was cultured by shaking it with a shaker at 37° C. for one hour.

The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids inserted thereinto bGH polyA DNA were selected and designated them as pCV4/CMV-bGH1.

(7-6) Preparation of Vector pEXP-BL2

To 1 ng of DNA sample Prepared through PCR amplification from Primers PB11 and PB12, 100 pmole of sense primer PB21 and anti-sense primer PB22 respectively, 2.5U (0.5 µl) of Taq polymerase (Takara Shuzo), 20 µl of PCR Buffer (250 mM Tris-HCl (pH 8.3 at 25° C.), 375 mM KCl, 15 mM $MgCl_2$), 1.0 µl of 100 mM DTT, 0.5 µl of 10 mM dNTP (10 mM dATP, dCTP, dGTP, dTTP) and 0.25 µl of acetylated BSA (4 mg/ml) were added, then were adjusted with the sterilized water to make its final volume 100 µl. One drop of the mineral oil (Sigma Chemical) was added to these mix solution, then PCR was performed according to the following condition. Namely, after the heat treatment for four minutes at 95° C., three steps treatment consisting of at 95° C. for one minute, at 55° C. for one minute and at 72° C. for two minutes were performed 30 times, and the reaction was terminated by the heat treatment for 10 minutes at 72° C. Liquid Phases were taken from this PCR reaction solution, and, to 10 µl of which, 2 µl of 10×H solution, 20U (1 µl) of the restriction enzyme BamHI as well as 20U (1 µl) of the restriction enzyme SpII and 7 µl of the sterilized water were added and it was reacted at 37° C. for one hour. The reaction solution was then applied to an electrophoresis employing 0.8% agarose-gel at 50 mA for 30 minutes. Approximately 0.47 kb band was detected by exposuring it to the ultraviolet rays of 360 nm wavelength and was excised.

These agarose fragments were poured into 1.5 ml tubes, then the tubes were centrifuged at 15,000 rpm for 10 minutes, and DNA solution was obtained by separating the solution so produced with a pipet.

Into 0.1 µl (1 ngDNA) of solution wherein Plasmid pCV4/CMV-bGH1 was treated with BglII and SpII, 0.5 µl of DNA solution noted above were added, then 2.0 µl of solution I attached to DNA ligation kit Ver.2 (Takara Shuzo) were further added, and these were reacted at 16° C. for 30 minutes. 0.1 ml of *Escherichia coli* competent cell XL1-BLUE (STRATAGENE) was added to the reaction-solution, then the solution was left on ice for 30 minutes to Proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so Produced, plasmids inserted thereinto the second bGH polyA DNA, namely, plasmids ((bGH polyA)$^2$) inserted thereinto and doubly bond to bGH polyA DNA were selected and designated them as cassette vector pEXP-BL2 having MCS cistron.

Figure 10:
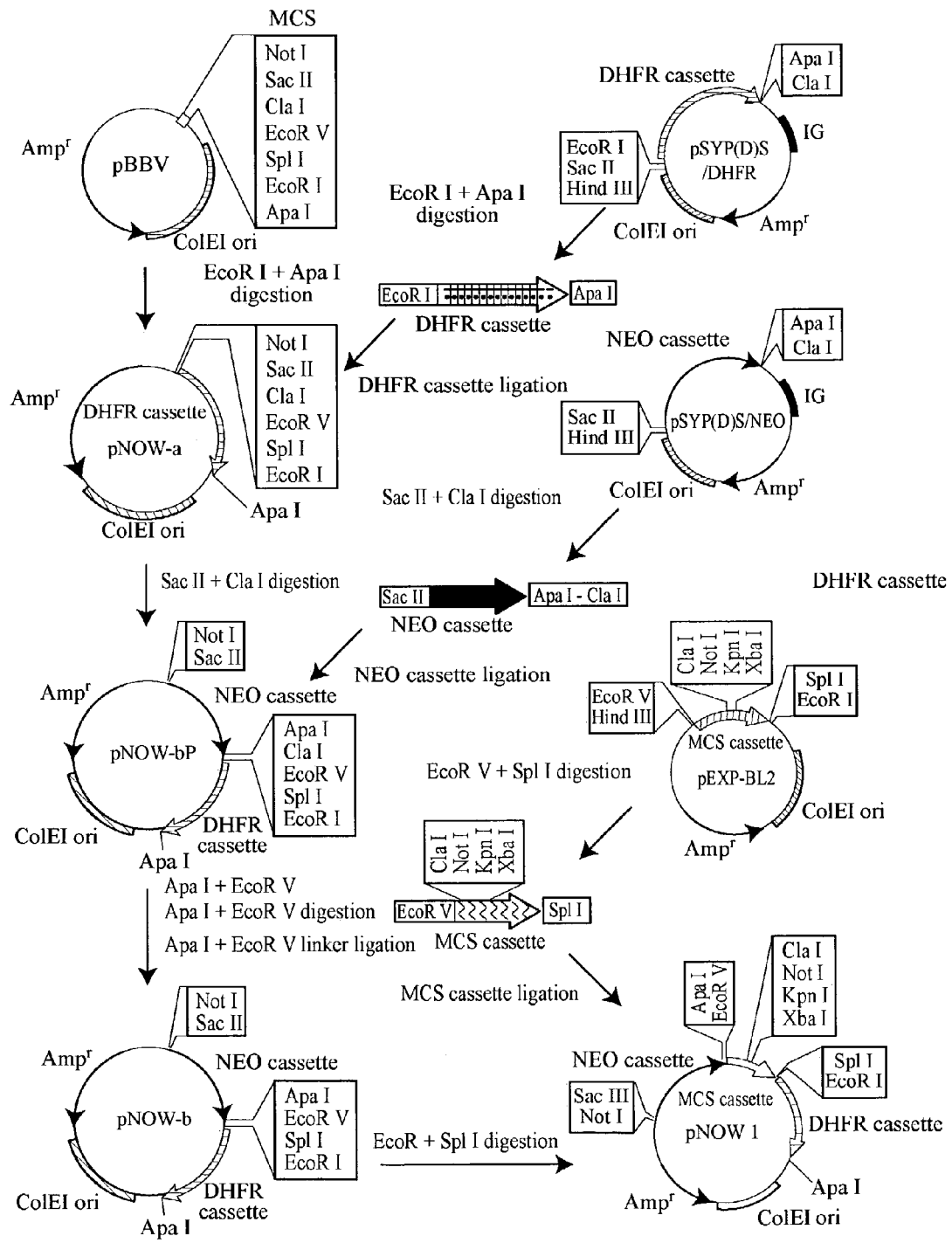
FIG. 10 shows a preparation scheme of Plasmid pNOW1.

(8) Preparation of Plasmid pNOW1 (FIG. 10)

(8-1) Preparation of Plasmid pNOW-a

To 100 ng (1 µl) of Plasmid pSVP(D)S/DHFR, 1 µl of 10×H solution was added, then, 20U (1 µl) of the restriction enzyme EcoRI and 20U (1 µl) of the restriction enzyme ApaI were further added, and these were reacted at 37° C. for one hour. The reaction solution was then applied to an electrophoresis employing 0.8% agarose-gel at 50 mA for 30 minutes. Approximately 1.75 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet. This DNA sequence constituted DHFR gene cistron and was consisted of $P_{SV40DE}$, Mu-DHFR (mutated) gene and SV40 polyA.

On the other hand, 1 ng (1 µl) of Plasmid pBBV to be inserted thereinto DNA sequence which constitutes DHFR gene cistron were treated with the restriction enzyme EcoRI and ApaI. 0.5 µl of solution containing DNA sequence which constitutes DHFR gene cistron were added to the solution containing the Plasmids so prepared, thereby, it was ligated between EcoRI and ApaI site. Into this reaction, 2.0 µl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin Plates containing 100 µg/ml ampicillin respectively.

After the overnight culture at 37° C., of the plasmids collected from the colonies so produced, plasmids additionally inserted thereinto DNA which constitutes DHFR gene cistron were selected and designated them as pNOW-a.

(8-2) Preparation of Plasmid pNOW-bp

To 100 ng (1 µl) of Plasmid pSVP(D)S/NEO, 1 µl of 10×H solution was added, then, 20U (1 µl) of the restriction enzyme SacII and 20U (1 µl) of the restriction enzyme ClaI were further added, and these were reacted for one hour. The reaction solution was then applied to an electrophoresis employing 0.8% agarose-gel at 50 mA for 30 minutes.

Approximately 2.4 kb band was detected by exposuring it to the ultraviolet rays of 360 nm wavelength and was excised.

These agarose fragments were poured into 1.5 ml tubes, then the tubes were centrifuged at 15,000 rpm for 10 minutes, and DNA solution was obtained by separating the solution so produced with a pipet. This DNA sequence constituted NEO gene cistron and was consisted of $P_{SV40DE}$, transposon sequence, Mu-NEO (mutated) gene and SV40 polyA.

On the other hand, 1 ng (1 µl) of Plasmid pNOW-a to be inserted thereinto DNA sequence which constitutes NEO gene cistron were treated with the restriction enzyme SacII and ClaI. 0.5 µl of solution containing DNA sequence which constitutes NEO gene cistron were added to the solution containing the plasmids so prepared, thereby, it was ligated between SacII and ClaI site. Into this reaction, 2.0 µl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded.

Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids additionally inserted thereinto DNA which constitutes NEO gene cistron were selected and designated them as pNOW-bp.

(8-3) Preparation of Plasmid pNOW-b

ClaI site was removed by substituting the newly synthesized ApaI-EcoRV linker for a serial sites of ApaI-ClaI-EcoRV to remove the ClaI site of multi-cloning site in Plasmid pNOW-bp so prepared. Firstly, as this linker, sense DNA having the base sequence of 5'-CGAT-3' and anti-sense DNA having the base sequence of 3'-CGGGCTA-5' were respectively synthesized. 1 ng (0.1 µl) of Plasmid pNOW-bp were digested with the restriction enzymes of ApaI and EcoRV. To the solution containing the plasmids so prepared, 100 pmole of ApaI-EcoRV linker sense DNA and anti-sense DNA respectively were added, then, 2.0 µl of solution I attached to DNA ligation kit Ver.2 (Takara Shuzo) were further added, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds. It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids additionally inserted thereinto DNA which constitutes NEO gene cistron were selected and designated them as pNOW-b.

(8-4) Preparation of Plasmid pNOW1

To 100 ng (1 µl) of Plasmid pEXP-BL2, 1 µl of 10×H solution was added, then, 20U (1 µl) of the restriction enzyme EcoRV and 20U (1 µl) of the restriction enzyme SplI were further added, and these were reacted for one hour. The reaction solution was then applied to an electrophoresis employing 0.8% agarose-gel at 50 mA for 30 minutes. Approximately 1.1 kb band was detected by exposuring it to the ultraviolet rays of 360 nm wavelength and was excised. These agarose fragments were poured into 1.5 ml tubes, then the tubes were centrifuged at 15,000 rpm for 10 minutes, and DNA solution was obtained by separating the solution so produced with a pipet. This DNA sequence constituted MCS cistron and was consisted of $P_{CMV}$, MCS-B and (bGH polyA)[2].

On the other hand, 1 ng (1 µl) of Plasmid pNOW-b to be inserted thereinto DNA sequence which constitutes MCS cistron were treated with the restriction enzyme EcoRV and SplI. 0.5 µl of solution on DNA sequence which constitutes MCS cistron were added to the solution containing the plasmids so prepared, thereby, it was ligated between EcoRV and SplI site. Into this reaction, 2.0 µl of solution I attached to DNA ligation kit Ver.2 (Takara Shuzo) were further added thereto, and these were reacted at 16° C. for 30 minutes. 0.1 ml of *Escherichia coli* competent cell XL1-BLUE (STRATAGENE) was added to the reaction-solution, then the solution was left on ice for 30 minutes to proceed the reaction followed by heat-shock at 42° C. for 60 seconds.

It had been left on ice for 2 minutes, then 0.9 ml of SOC medium (Toyobo) was added thereto and was cultured by shaking it with a shaker at 37° C. for one hour. The solution was centrifuged at 5,000 rpm for one minute, the supernatant was then discarded. Deposited competent cells were suspended with the solution remained in the centrifugation tube, then these were inoculated at the ratio of 1:10 into two ampicillin plates containing 100 µg/ml ampicillin respectively. After the overnight culture at 37° C., of the plasmids collected from the colonies so produced, plasmids inserted thereinto DNA which constitutes MCS cistron were selected and designated them as pNOW1.

Structure of Plasmid pNOW1 is shown in FIG. 11. Then. whole base sequences of Plasmid pNOW1 is set out in SEQ. ID. NO:25.

EXAMPLE 2

Construction of Expression Vector pNOW1-hMBP

First of all, hMBP sequences from its initiation codon to its stop codon were amplified from human liver cDNA library (Clontech) with a zymoreacter (Atto) by using the primer having the base sequence of AAGGAAAAAAGCG-GCCGCATGTCCCTGTTTCC ATCACTC (SEQ. ID. NO:26) and that having the base sequence of GCTCTA-GATCAGATAGGGAACTCACAGAC (SEQ. ID. NO:27).

hMBP cDNA so obtained were digested with the restriction enzymes of NotI and XbaI, and cDNA corresponding to 66~812 bp in such cDNA (SEQ. ID. NO:2) so obtained were employed as an insert.

Figure 12:
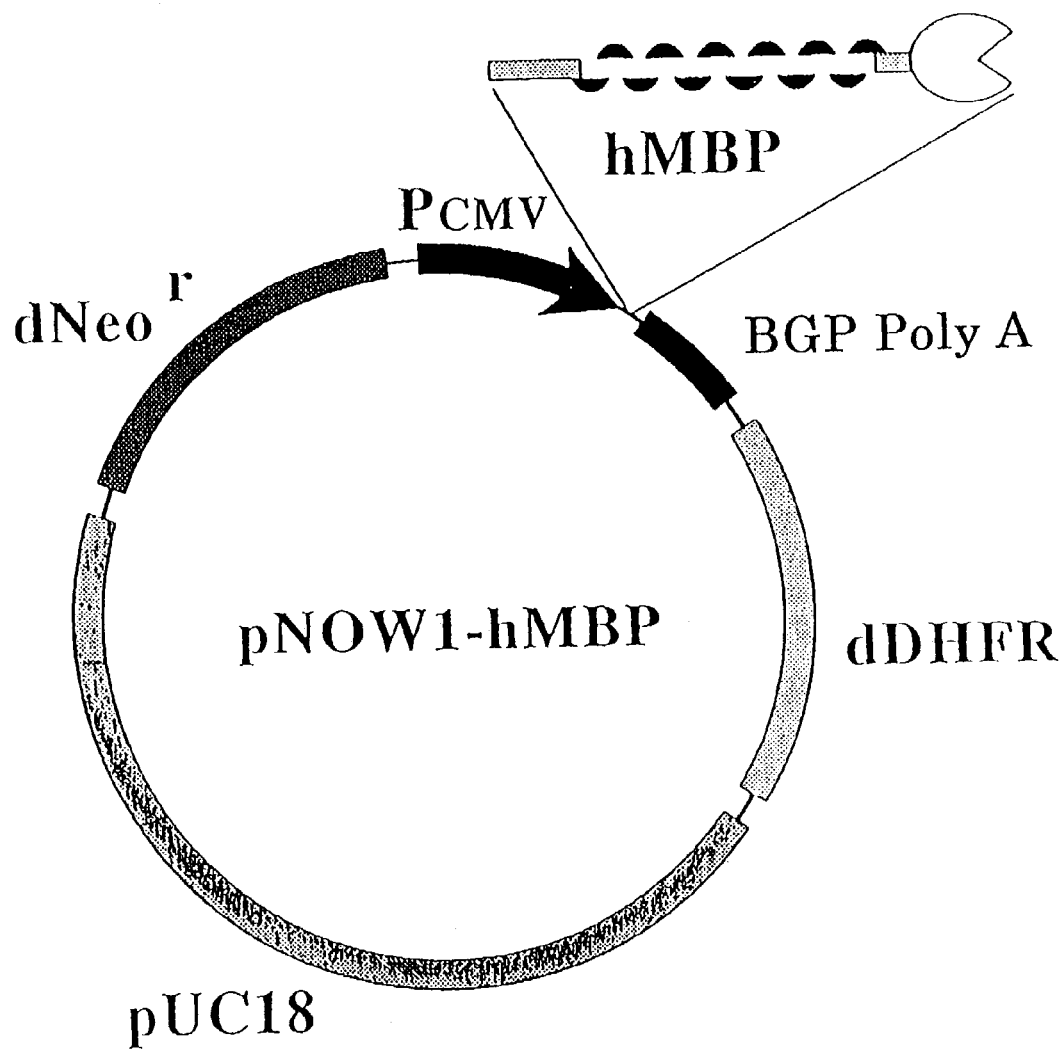
FIG. 12 is a schematic view on the structure of Plasmid pNOW1-hMBP.

Then, the expression vector pNOW1 prepared in Example 1 was digested with the restriction enzymes of NotI and XbaI, and said insert was inserted with DNA ligation kit (Takara Shuzo) into the downstream of cytomegalovirus promoter (pCMV), namely,between pCMV and BGP polyA (corresponding to (bGHpA)² in FIG. 11). The expression vector so prepared was designated as Plasmid pNOW1-hMBP, and its structure is illustrated as schematic view in FIG. 12.

EXAMPLE 3

Selection of Expression Clone (1) Introduction of Expression Vector pNOW1-hMBP into Chinese Hamster Ovar (CHO) cells lacking Dihydrofolate Reductase (dhfr⁻)

Iscove's Modified Dulbecco's Medium (IMDM;GIBCO) not contained therein hypoxanthine and thymidine but supplemented thereto 10% bovine fetal serum (FCS, GIBCO) was Prepared, then DG44 CHO cell strain lacking DHFR gene continued for two weeks under the condition at 37° C. and 5% $CO_2$, 84 wells of 960 wells have active cells, and there were G418 resistance cells (clones).

When the Productivities of hMBP by such G418 resistance clones were studied, most of G418 resistance clones exhibit high productivity on hMBP.

Figure 13:
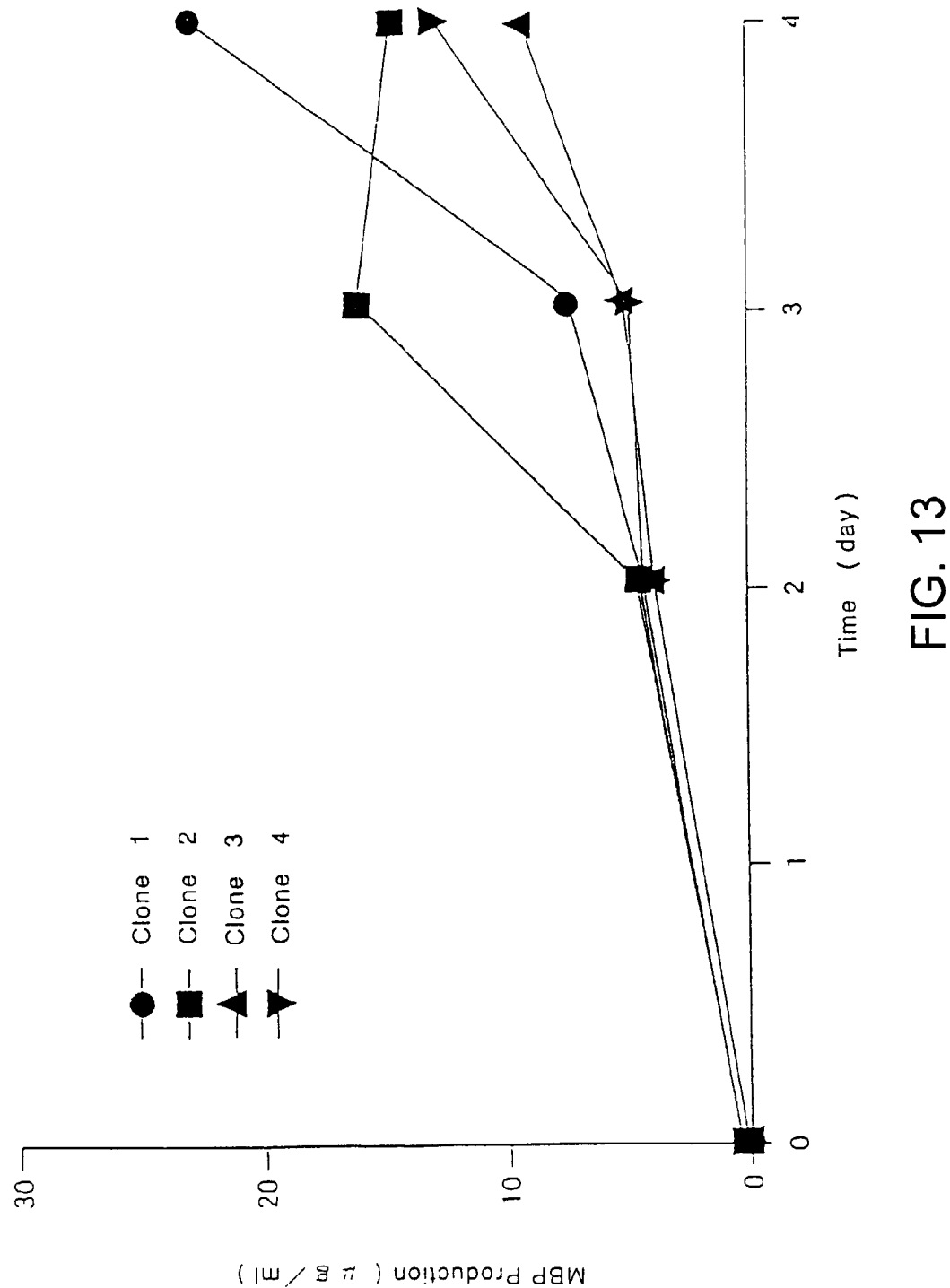
FIG. 13 is a graph showing production of rhMBP in the neomycin (G418) resistance clone.

Some clones were selected from the clones having the demonstrated hMBP productivities and were inoculated into 25 cm² culture flask. Cultivation were continued until density of the cells were increased, and the cell number measured at that moment was $3 \times 10^6$ cells/25 cm² culture flask. Culture supernatant from each of culture flasks were discarded, then 2 ml of IMDM supplemented thereto 10% FCS were added thereto wherein components of such IMDM were identical to IMDM previously noted, and culture were performed for four days, thereafter, culture supernatant so obtained were collected. When amount of hMBP (rhMBP) in the collected culture supernatant were measured, there were production of over 5 µg/ml in some culture flasks. Amounts of hMBP were quantified with regard to the native MBP as a control, anti-rabbit polyclonal antibody (expressed in *Escherichia coli*) for carbohydrate recognition domain (CRD) and neck region in the collectin and hMBP (subjects to be quantified), along with the method of Suzuki et al., (Y. Suzuki, et al., "Characterization of Recombinant Bovine Conglutinin Expressed in a Mammalian Cell", *Biochem Biophys. Res. Commun.*, 238, pp.856–863 (1997)). Results on four clones having high productivities are shown in the graph of FIG. 13. hMBP production by the clone having the highest productivity was 23.3 µg/ml.

(3) Production of MTX Resistance CHO Cells

After stabilizing the hMBP production clones by further subculturing them, gene amplification was performed with a medium supplemented thereto the low concentration MTX.

Firstly, each of the selected two cell clones were mixed with IMDM supplemented thereto 10% dialyzed FCS (JRH Bioscience) and contained 5 nM MTX and 400 µg/ml of Neomycin (G418), thereafter, amount of 0.1 ml/well of which were inoculated (poured) into 10 pieces of 96-well microplate. When the culture had been continued for two weeks under the condition at 37° C. and 5% $CO_2$, most of 960 wells have active cells, and there were 5 nM MTX resistance cells (clones). When the productivities of hMBP by such 5 nM MTX resistance clones were studied, most of 5 nM MTX resistance clones exhibit high productability on hMBP. Five clones were optionally selected from such clones, then each of which were inoculated into 25 cm² culture flasks, and the culture were continued until density of the cells were increased.

Figure 14:
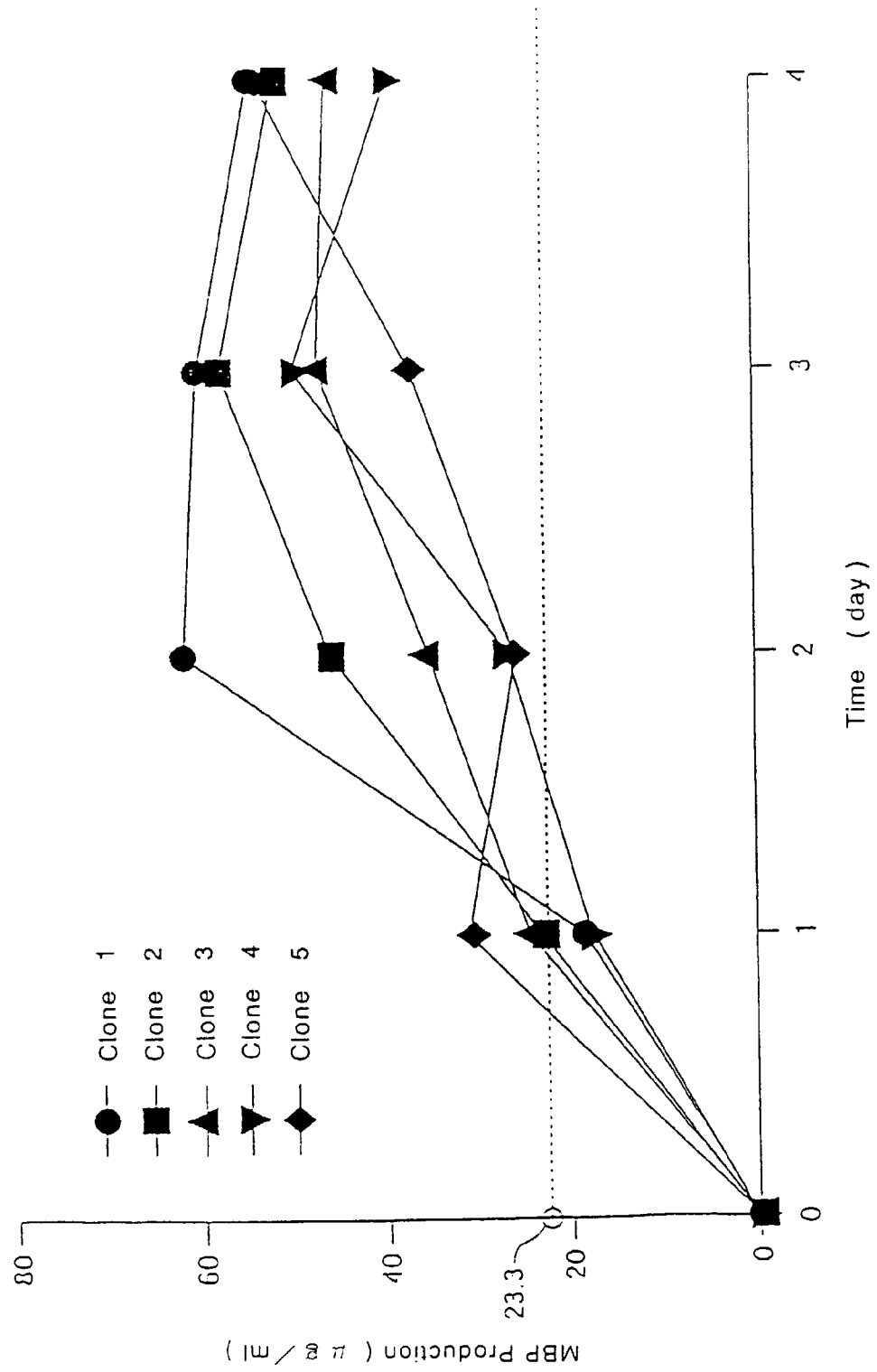
FIG. 14 is a graph showing production of rhMBP in the MTX resistance clone.

Culture supernatants were discarded, then 2 ml of IMDM (supplemented thereto 5 nM MTX and 400 µg/ml of G418) were added thereto, and culture were performed for four days, thereafter, culture supernatant so obtained were collected and production level of hMBP were measured. Amounts of hMBP were quantified according to the similar method noted in Example 3(1). Results are shown in the graph of FIG. 14. hMBP Production by the clone having the highest productivity was 54.1 µg/ml.

EXAMPLE 4

Analysis of Structure of rhMBP by PAGE Analysis and Gel-Filtration Chromatography (1) Purification of rhMBP The clone having the highest productivity in the clones so produced was inoculated into 225 cm² culture flask and was the culture were continued until density of the cells were increased. Then, the culture supernatants were discarded, then 50 ml of CHO-S-SFM II medium (vitamin C was added to be the final concentration of 100 mM if it is added) containing 5 nM MTX and 400 µg/ml of G418 were added thereto, and culture were performed for four days. Culture supernatant so obtained were collected and was dialyzed to TBS (prepared from TBS Powder (Takara Shuzo)), thereafter, it was dialyzed to TBSC (5 mM $CaCl_2$, TBS).

Next. it was purified by mannan-agarose (SIGMA). Namely, mannan-agarose were packed in column (Column PD-10, Empty, Pharmacia), then the dialyzed culture solution were passed therethrough, were washed with TBSC and were eluted with TBSE (10 mM EDTA, TBS). After such elution, 1M $CaCl_2$ were added thereto to be its final concentration of 15 mM, then the solution were applied again to the mannan-agarose, then were washed with TBSC and were eluted with TBS containing 100 mM mannose, thereafter, the purified rhMBP products were produced by re-dialyzing such re-eluted solution to TBSC.

Figure 15:
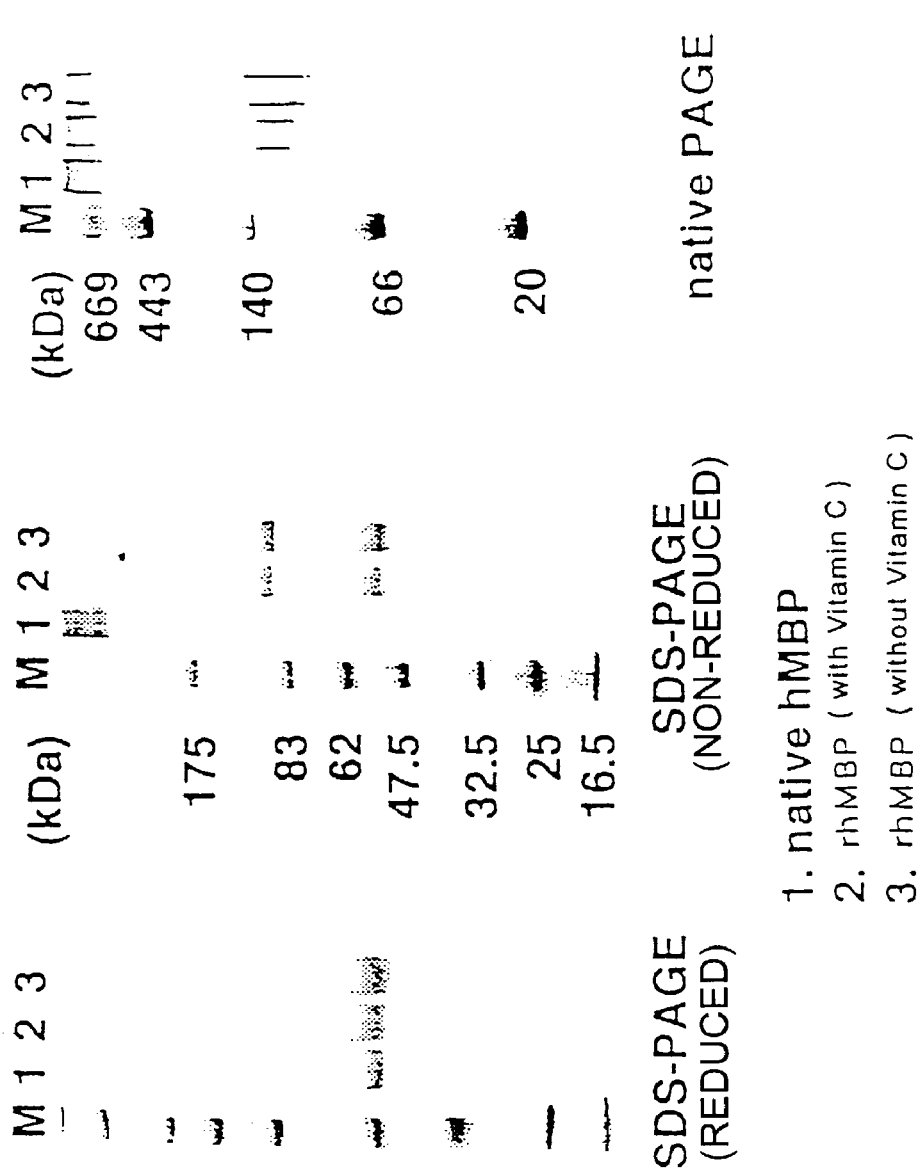
FIG. 15 shows results of PAGE analysis on rhMBP.

(2) PAGE Analyse of Purified rhMBP hMBP produced in Example 4(1) were analyzed by PAGE. SDS-PAGE employed polyacrylamide gel (Daiichi Pure Chemical) having the concentration gradient of 4~20% under the non-reducing condition, polyacrylamide gel (Daiichi Pure Chemical) having the concentration gradient of 10~20% under the reducing condition and Polyacrylamide gel (Daiichi Pure Chemical) having the concentration gradient of 4~20% for the native PAGE. Polypeptides were stained with 1% Coomassie Blue (CBB). Results thereof are shown in FIG. 15. In FIG. 15, Lane M is the molecular weight marker (prestained protein marker broad range (NEW ENGLAND BIO Labs)), Lane 1 is the native hMBP, Lane 2 is rhMBP (cultured with vitamin C) and Lane 3 is rhMBP (cultured without vitamin C).

As shown in FIG. 15, although there was band at the molecular weight which is same to the native hMBP on SDS-PAGE under the reduction condition, there were bands pattern of which are different from those of the native hMBP on SDS-PAGE under the non-reducing condition and the native PAGE.

(3) Gel-Filtration Chromatography Analysis of Purified rhMBP

Purified rhMBP were gel-filtrated with Superose™ 6 HR10/30 medium (ø10 mm×300 mm length; Pharmacia) at flow rate of 0.5 ml/min using 20 mM Tris-HCl (pH 8.0), 0.15 NaCl, 5 mM EDTA. 40 µg of rhMBP was applied on this column and was measured at 280 nm absorbance.

Figure 16:
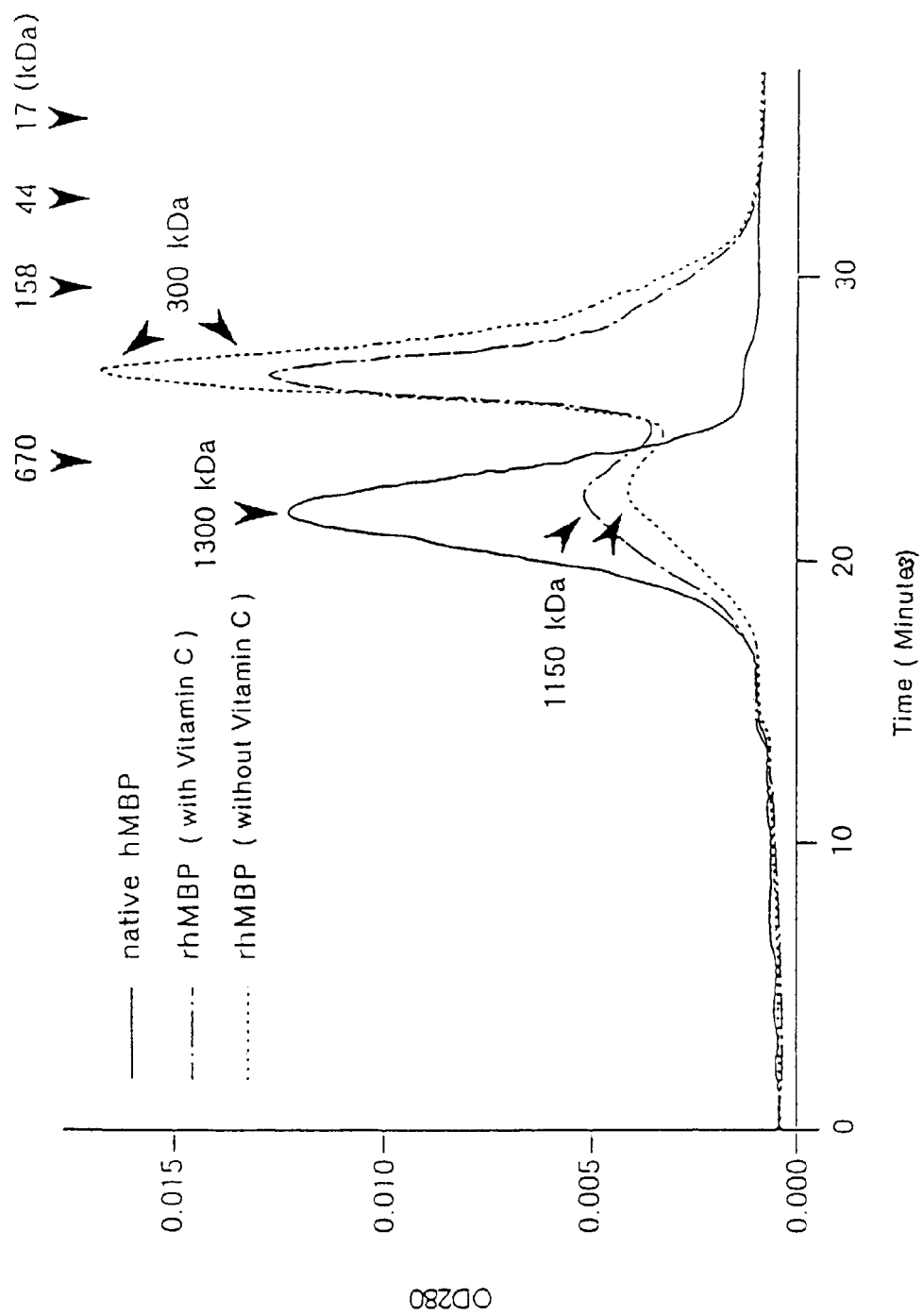
FIG. 16 is a graph showing results of gel-filtrations on rhMBP.

Gel-Filtration Standard (thyroglobulin (670 kDa), bovine γ-globulin (158 kDa), chicken ovalbumin (44 kDa), bovine myoglobulin (17 kDa) Bio-Rad) were employed for calibration of the column. As shown in FIG. 16, there were major peaks at 300 kDa in rhMBP and at 1,300 kDa in the native hMBP.

EXAMPLE 5

Sugar Binding Activities and Sugar Binding Specificities by rhMBP and Native hMBP Microtiter Plates were treated with 100 µA of coating buffer (15 mM sodium carbonate, 35 mM sodium hydrogen carbonate, 0.05% sodium azide, pH 9.6) containing mannan (10 µg/ml:SIGMA) at 4° C. overnight. After each treatment step, the plates were washed three times with TBSNTC solution (TBS, 0.05% sodium azide, 0.05% Tween 20 (Registered Trade Mark), 5 mM calcium chloride). After completing the coating of the plates, the plates were treated and blocked with BlockAce™ blocking solution (Dainippon Pharmaceutical) at room temperature for one hour.

After washing them, samples of stepwise dilution of the native hMBP, rhMBP (cultured with vitamin C), rhMBP (cultured without vitamin C) having the concentration of 200, 100, 50, 25, 12.5, 6.25 ng/ml, combination samples of 200 ng/ml of each hMBP with EDTA added to be its concentration of 10 mM, and combination samples of 50 ng/ml of each hMBP with mannose added to be its concentration of 100 mM were prepared, thereafter, 100 µl of each of them were poured into each well and were incubated at 37° C. for one hour. After washing them, biotinylated anti-rabbit anti-hMBP antibody (biotinylated with EZ-Link (Registered Trade Mark) Sulfo-NHS-LC-Biotin (PIACE)) diluted 1,000 times with TBSNTC were added thereto, then they were incubated at 37° C. for one hour and were washed. Then, a complex of avidin and biotinylated alkaline phosphatase was formed at 37° C. for 30 minutes with VECTASTAIN ABC-AP STANDARD KIT (VECTOR) and was washed. Finally, 100 µl of TMB substrate solution (TMB Microwell Peroxidase Substrate System: KPL) were added to each well. After incubating them at room temperature for 30 minutes, 100 µl of 1M phosphoric acid were added thereto, and their absorbance were measured at 450 nm (Model 450 Microplate Reader; Bio-Rad), Then, evaluation on sugar inhibiting activities were performed according to the method of Lu et al., (Biochem. J., Vol.284, pp.795–802 (1992)) employing this ELISA system.

After coating the microliter plates with mannan (1 µg/100 µl well), the native hMBP and rhMBP (cultured with or without vitamin C) were reacted under the co-presence of the sugars in their final concentration of 100, 50, 25, 12.5, 6.3, 3.1, 1.6 mM. Sugar binding specificity was indicated as $I_{50}$ with regard to sugar concentration necessary to halve binding activities in comparison with the suppression curve. Results thereof are shown in the following Table 1.

TABLE 1

Sugar Binding Specificities on rhMBP and native hMBP

| | $I_{50}$ (mM)* | | |
|---|---|---|---|
| Sugars | native hMBP | rhMBP (with Vitamin C) | rhMBP (without Vitamin C) |
| N-Acetyl-D-Glucosamine | 2.7 | 3.6 | 3.8 |
| L-Fucose | 4.2 | 4.4 | 8.7 |
| D-Fucose | 33.5 | 39.1 | 86.7 |
| D-Mannose | 3.7 | 6.7 | 6.8 |

TABLE 1-continued

Sugar Binding Specificities on rhMBP and native hMBP

| | $I_{50}$ (mM)* | | |
|---|---|---|---|
| Sugars | native hMBP | rhMBP (with Vitamin C) | rhMBP (without Vitamin C) |
| Maltose | 7.4 | 6.4 | 7.4 |
| N-Acetyl-D-Mannosamine | 4.4 | 6.9 | 6.9 |
| Glucose | 3.2 | 2.0 | 2.4 |
| Galactose | 24.2 | 29.8 | 36.7 |
| N-Acetyl-D-Galactosamine | >100 | >100 | >100 |
| Lactose | 36.0 | 46.6 | 59.4 |

*Sugar concentration to halve binding activities with mannan

Figure 17:
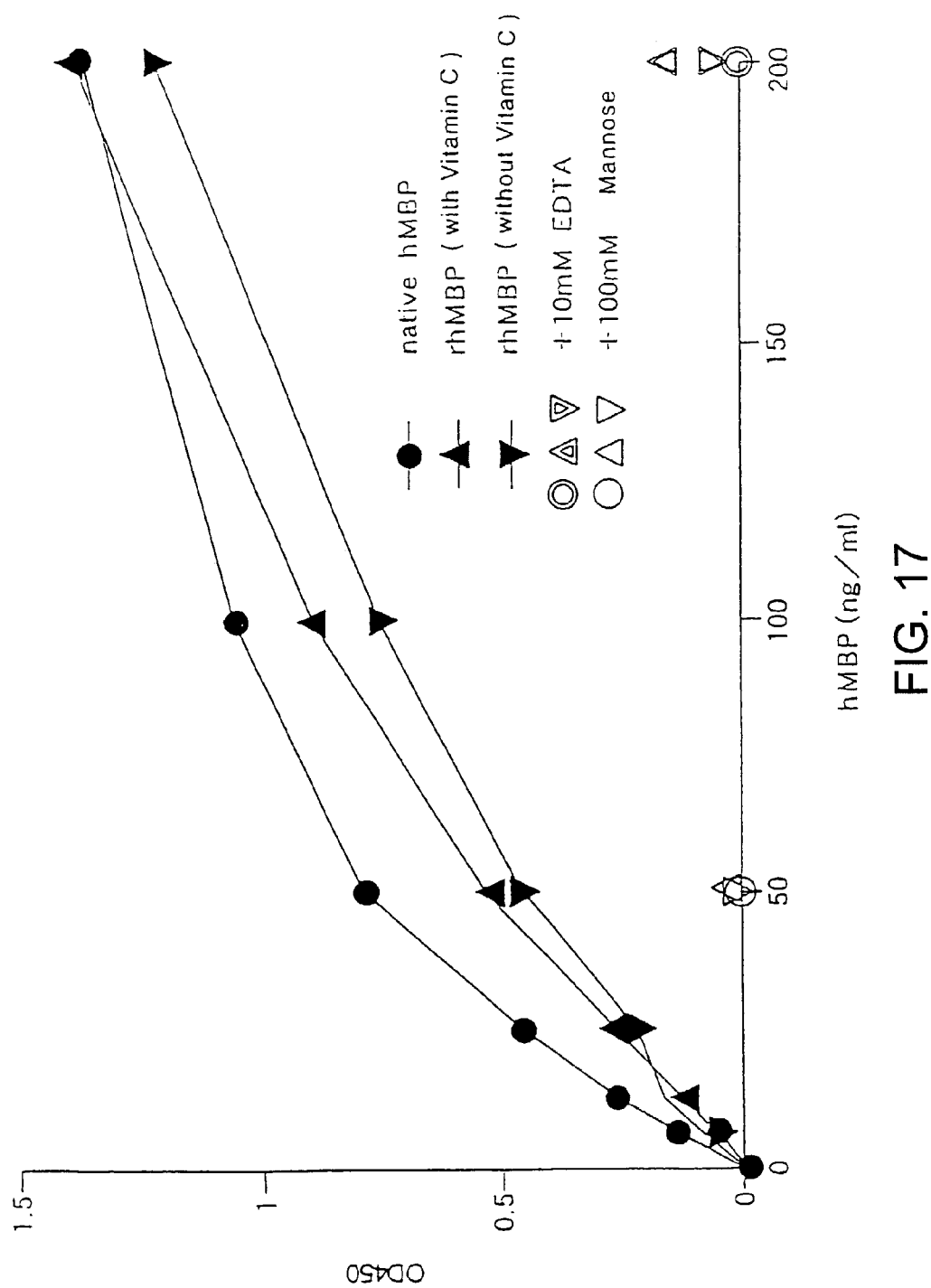
FIG. 17 is a graph showing glyco-binding activities on rhMBP and native hMBP.

Apparently from the results shown in Table 1, sugar binding specificities by rhMBP are substantially identical to those by the native hMBP. Then, as shown in FIG. 17, sugar binding activity by rhMBP are similar to those by the native hMBP.

EXAMPLE 6

Hemagglutination Inhibition (HI) Activities (1) Viruses

Influenza A virus A/Ibaraki/1/90 (H3N2: Influenza A virus (A-Hong Kong)) were used to evaluate Hemagglutination Inhibition (HI) Activities.

Viruses were subcultured 40 times with CAM (chorioallantoic membrane) from the matured egg according to the standard method and were stored at −70° C. until use. As a growth medium for the viruses, Eagle MEM medium (Nissui Pharmaceutical) containing 3% vitamin for tissue culture, 0.2% albumin, 0.1% glucose and 0.22 ng/ml acetylated trypsin was used.

(2) Hemagglutination Inhibition (HI) Activities by rhMBP

In accordance with the method of Okuno et al.,(J. Clin. Microbiol., Vol.28, pp.1308–1313 (1990)), Hemagglutination Inhibition (HI) activities were determined. Namely, native hMBP and rhMBP (cultured with or without Vitamin C) (5 µg/ml) were diluted double-stepwise with 25 µl of TBSC on 96-well microplates. 25 µl of 16HAU (Hemagglutination Unit) virus solution were added to each of MBP solution diluted stepwise, then were reacted at 37° C. for 60 minutes, and 50 µl of 0.5% chicken's erythrocytes solution were added thereto. After the incubation at 4° C. for 60 minutes, effects on rhMBP against viral hemagglutination on chick's erythrocytes were observed. Results are shown in the following Table 2 and FIG. 18.

TABLE 2

Minimum Protein Concentration (ng/ml) for Hemagglutination Inhibition (HI) Activities by rhMBP and native hMBP

| | Minimum Protein Concentration (ng/ml) for HI Activities |
|---|---|
| native hMBP | 40 |
| rhMBP (with Vitamin C) | 80 |
| rhMBP (without Vitamin C) | 80 |

Figure 18:
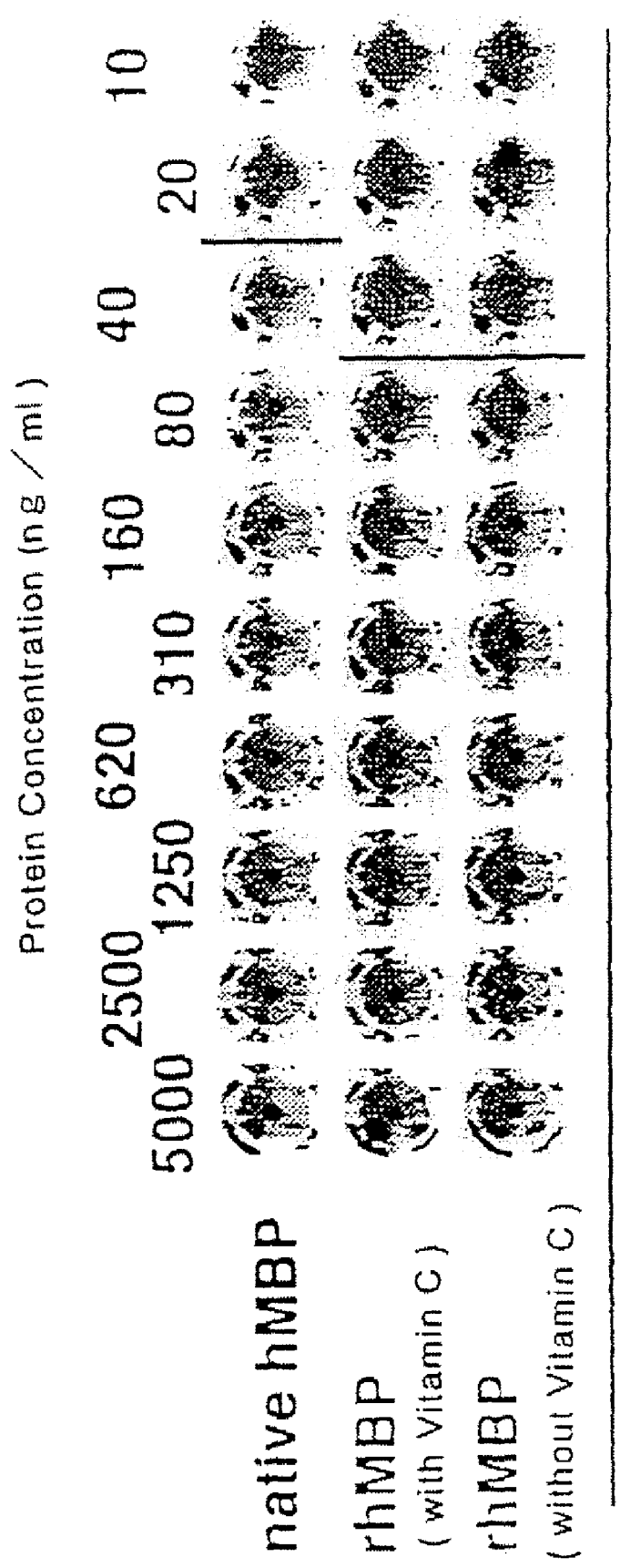
FIG. 18 shows activities by rhMBP on Hemagglutination Inhibition (HI).

Results shown in Table 2 and FIG. 18 indicated that Hemagglutination Inhibition (HI) activities by rhMBP are not inferior to that by native hMBP.

EXAMPLE 7

Neutralization Activities (1) Viruses

Influenza A virus A/Ibaraki/1/90 employed in Example 6 were used.

(2) Neutralization Activities

Neutralization Activities were evaluated according to the method of Okuno et al., (J. Clin. Microbiol., Vol.28, pp. 1308–1313 (1990)). The native hMBP and rhMBP (cultured with or without vitamin C) were diluted double-stepwise with TBSC and were mixed equivalently with viral solution of 50 Focus Forming Unit (FFU)/25 µl, thereafter, they were reacted at 37° C. for 60 minutes. 50 µl of these reaction solution were inoculated into three wells per each concentration of MBP dilution on 96-well microplates wherein Madin-Darby Canine Kidney (MDCK) cells were monolayer cultured in Eagle MEM medium containing 10% bovine fetal serum (GIBCO). After incubating them at 35° C. for 60 minutes, cells were washed and were added thereto growth medium for influenza viruses containing 0.5% tragacanth gum (Wako Pure Chemical Industries), thereafter. they were cultured for 24 hours in $CO_2$ incubator.

After the culture, cells were washed and were fixed with ethanol. After air-drying the cells, they were reacted with each of anti-influenza hyperimmune rabbit serum, anti-rabbit IgG goat serum (ICN Pharmaceuticals) and Peroxidase anti-peroxidase (rabbit) complex (ICN Pharmaceuticals) at 37° C. for 30 minutes. After washing them with PBS, DAB solution (SIGMA) were added thereto, and reaction was continued until color of the virus-infected focus are changed to reddish-brown. Then, after washing them with tap water and air-drying the same, number of virus-infected focus were counted.

Figure 19:
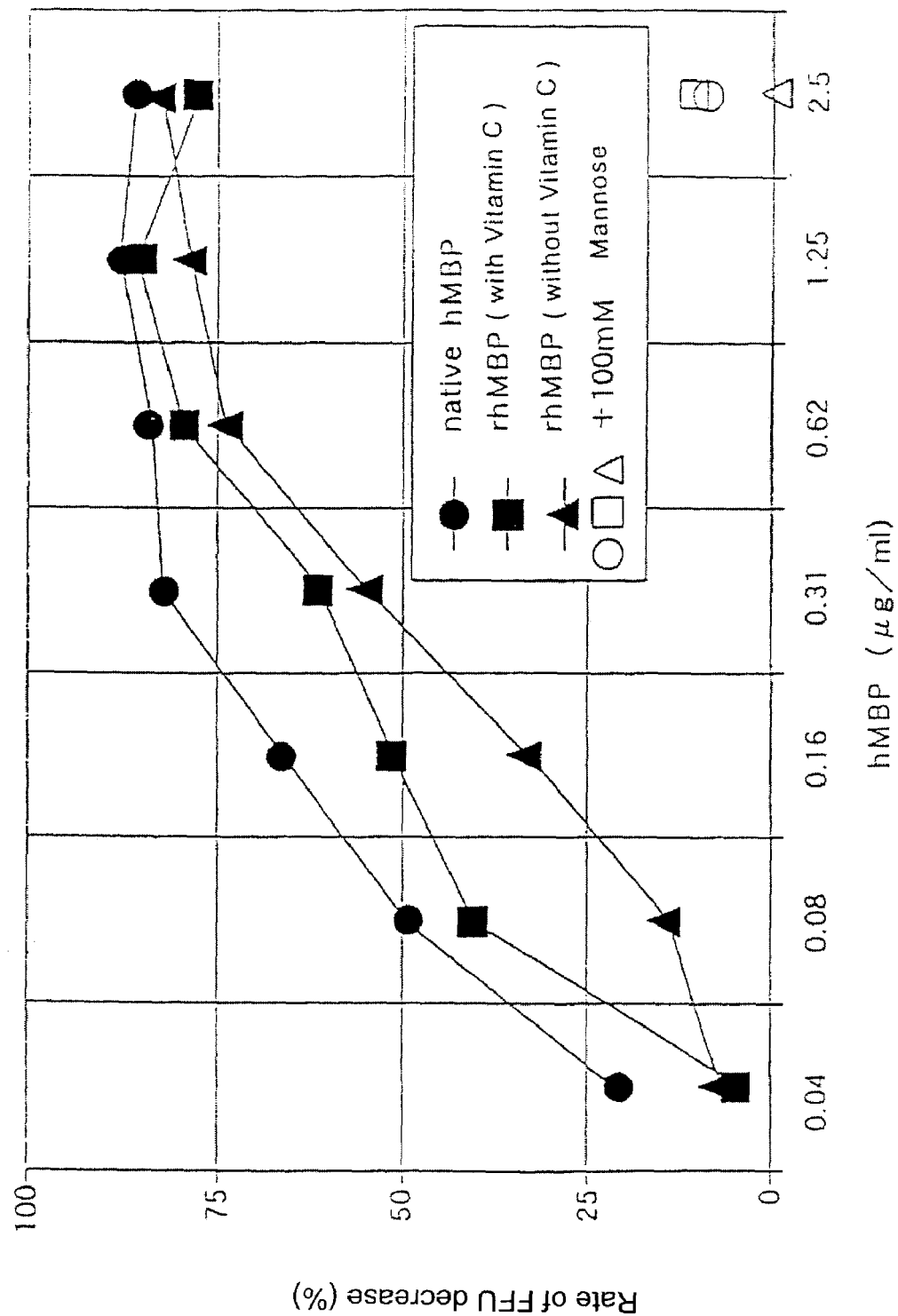
FIG. 19 is a graph showing activities by rhMBP to neutralize an infection of Influenza A virus.

FIG. 19 shows results obtained by comparison on the neutralization activities for influenza A viruses in the native hMBP, rhMBP fraction (cultured in the medium containing vitamin C), rhMBP fraction (cultivated in the medium without vitamin C) and said fractions combined these with 100 mM mannose. Neutralization titer were indicated as reduction rate of FFU based on 100% counts obtained, instead of MBP, from mixture of viral solution and TBSC only. As a result thereof, similar to the native hMBP, rhMBP (cultured with or without vitamin C) had neutralization activities for influenza virus, and such activities were inhibited by addition of mannose.

(3) Binding Activities to HIV-1, HBV and Influenza A Virus

Binding activities on rhMBP to HIV-1, HBV and Influenza A virus were determined by electrophoresing the following viral structural proteins, transferring them to membranes, binding thereto rhMBP and detecting them with labeled antibody.

Necessary amounts of viral structural proteins for the electrophoresis were 0.25 µg of HIV-gp120 ($HIV_{IIIB}$-gp120) (ADVANCED BIOTECHNOLOGIES INCORPORATED (ABI)), 0.25 µg of HIV-gp160 ($HIV_{IIIB}$-gp160) (ABI), 10 µg of HBS (Hepatitis B Surface Antigen (HBsAg)(ABI), Subtype ad), Influenza A virus (IAV; presented by The Research Foundation For Osaka University Research Institute for Microbial Diseases), 5 µg of H1N1 Yamagata virion and 5 µg of H3N2 Beijin virion.

SDS-PAGE employed polyacrylamide gel having the concentration gradient of 4~20%, and HIV-1 and HBS were electrophoresed under reducing condition. After the electrophoresis, they were transferred to Immobilon-P$^{SQ}$ transfer membrane (Millipore) with Nova Blot™ electrophoretic transfer unit (Pharmacia) by using semi-dry electroblot buffer kit (Owl Scientific). After such transfer, they were blocked with BlockAce™ blocking solution (Dainippon Pharmaceutical) at room temperature for one hour. Then they were washed three times for 10 minutes with TBSTC (0.05% Tween 20 (Registered Trade Mark), 5 mM $CaCl_2$, TBS) or TBSTE (0.05% Tween 20 (registered Trade Mark), 5 mM EDTA, TBS) (control which inhibits calcium ion ($Ca^{2+}$) dependent binding to carbohydrate recognition domain of rhMBP), and the solution diluted rhMBP to 1.0 µg/ml with TBSTC or TBSTE were reacted at room temperature for one hour.

In accordance with said procedure, after washing them with TBSTC or TBSTE, anti-human MBP polyclonal antibody diluted 1000 times with TBSTC were added thereto, and they were reacted at room temperature for one hour. After washing them with TBSTC, anti-rabbit IgG alkaline phosphatase label (Chemicon International) diluted 5000 times with TBSTC were added thereto, and they were reacted at room temperature for 30 minutes. After washing them with TBSTC, color were developed with NBT/BCIP (GIBCO).

Figure 20:
FIG. 20 is a graph showing activities by rhMBP to bind it to HIV-1, HBV and Influenza A virus.

Results are shown in FIG. 20. As shown in FIG. 20, it was demonstrated that the present rhMBP have binding activities to any of HIV-1, HBV and Influenza A virus.

EXAMPLE 8

Viral Growth (Infection Spread) Inhibition Activities (1) Viruses

Influenza A virus A/Ibaraki/1/90 employed in Example 6 were used.

(2) Viral Growth (Infection Spread) Inhibition Activities

MDCK cells were monolayer cultured in Eagle MEM medium containing 10% bovine fetal serum (GIBCO) on 24-well microtiter plates and influenza viruses were inoculated thereinto to be 30 FFU per well. After incubating them at 35° C. for 60 minutes, cells were washed and were added thereto 1 ml/well growth medium for influenza viruses containing 0.5% tragacanth gum. Further, native hMBP, rhMBP (cultured with vitamin C), rhMBP (cultured without vitamin C), bovine serum albumin were added thereto to be 0.5 µg/ml and 1 µg/ml per well, and they were cultured for three days.

Figure 21:
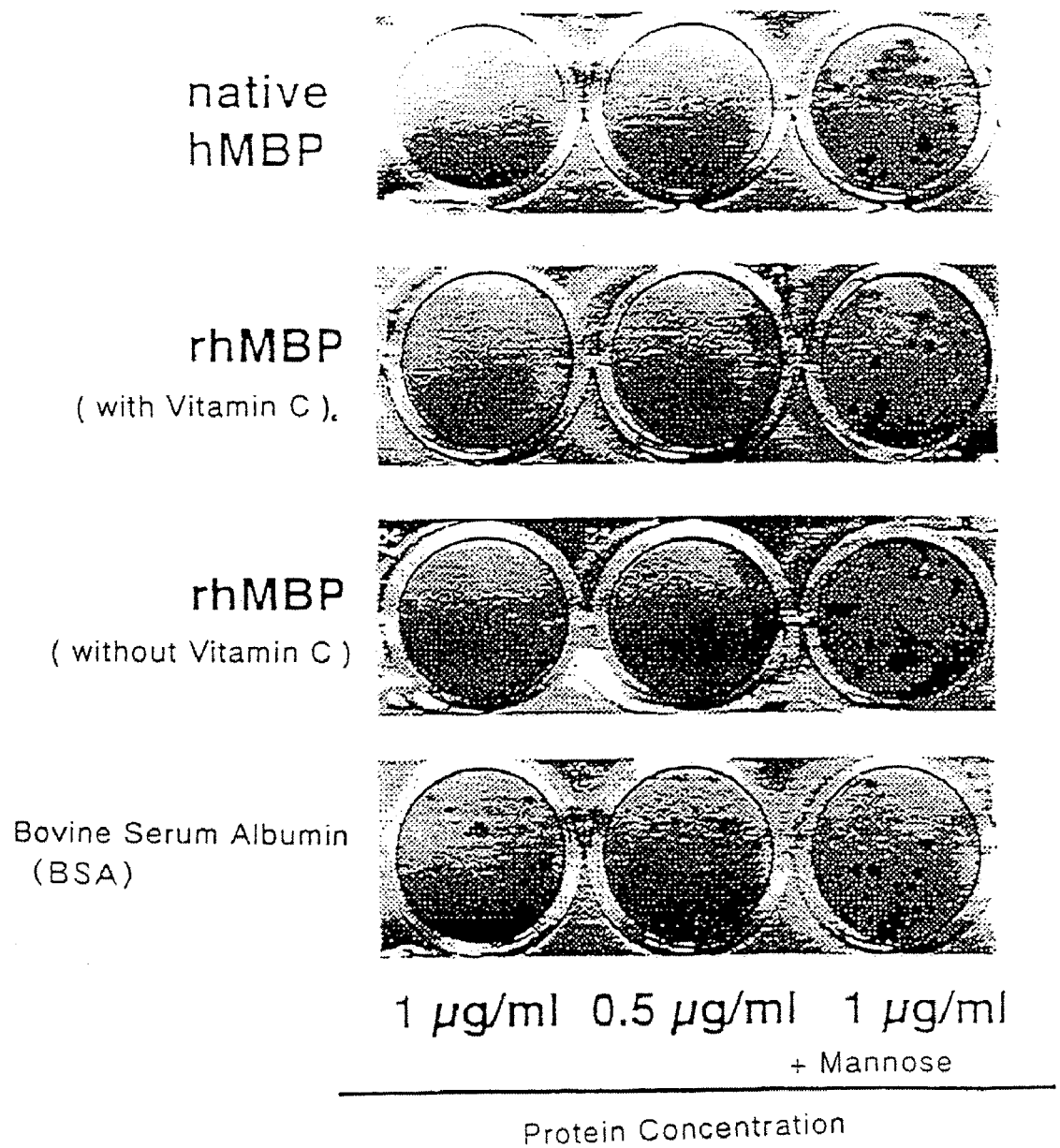
FIG. 21 shows activities by rhMBP to inhibit viral growth (infection spread).

After washing the cells, similar steps were taken along with Neutralization Activities of Example 7 (2), gross area of the virus-infected focus were determined with PAP staining. Results thereof are shown in FIG. 21. As a control, samples cultured under the co-presence of 100 mM mannose were employed (Right Column in FIG. 21). Apparently from the results shown in FIG. 21, rhMBP reduced focus area infected by influenza viruses concentration-dependently and exhibited an inhibition effect on viral growth.

EXAMPLE 9

Activities on rhMBP for Activating Complement (1) Viruses

As influenza A virus, A/Ibaraki/1/90 (H3N2) employed in Example 6 were used.

(2) Preparation of Sensitized Sheep Erythrocyte

After washing Sheep Erythrocyte (Japan Biotest Institute) with gelatin-veronal buffer (1×veronal (145 mM NaCl, 15.6 nM 5,5-diethyl barbituric acid. 9.09 mM 5,5-diethyl sodium barbiturate), 1% gelatin, 0.25 mM $CaCl_2$, 0.82 mM $MgCl_2$), they were diluted with gelatin-veronal buffer to be its concentration of $1\times10^9$ cell/ml. After mixing them with 10 ml of Sheep Erythrocytet ($1\times10^9$ cell/ml), 5 ml of chromium chloride (0.5 mg/ml) and 5 ml of mannan (60 μg/ml), then were incubated at room temperature for five minutes, and sensitized sheep erythrocyte were prepared by washing them several times with gelatin-veronal buffer and suspending the same into gelatin-veronal buffer to be readjusted its concentration of $1\times10^9$ cell/ml.

(3) Activation of Complement

400 μl of each of native hMBP and rhMBP (cultured with or without vitamin C) and 100 μl of sensitized sheep erythrocyte were mixed thereamong, the mixture so produced were incubated at room temperature for 15 minutes (each lectin concentration were 1, 10, 100 and 1000 ng/tube as a final concentration).

After the centrifugation, deposits were suspended in 1.1 ml of veronal buffer. 400 μl of guinea pig complement (ICN Pharmaceuticals: immanent MBP of which were removed with mannan-column and diluted 20 times with gelatin-veronal buffer) were added thereto, and they were incubated at 37° C. for 60 minutes and absorbance on supernatant were measured at 541 nm. Control was completely hemolyzed erythrocyte prepared by adding 1400 μl of distilled water to 100 μl of sensitized sheep erythrocyte. In an experiment on inhibition by mannose, sensitized sheep erythrocyte and hMBP were simultaneously added at the reaction.

Figure 22:
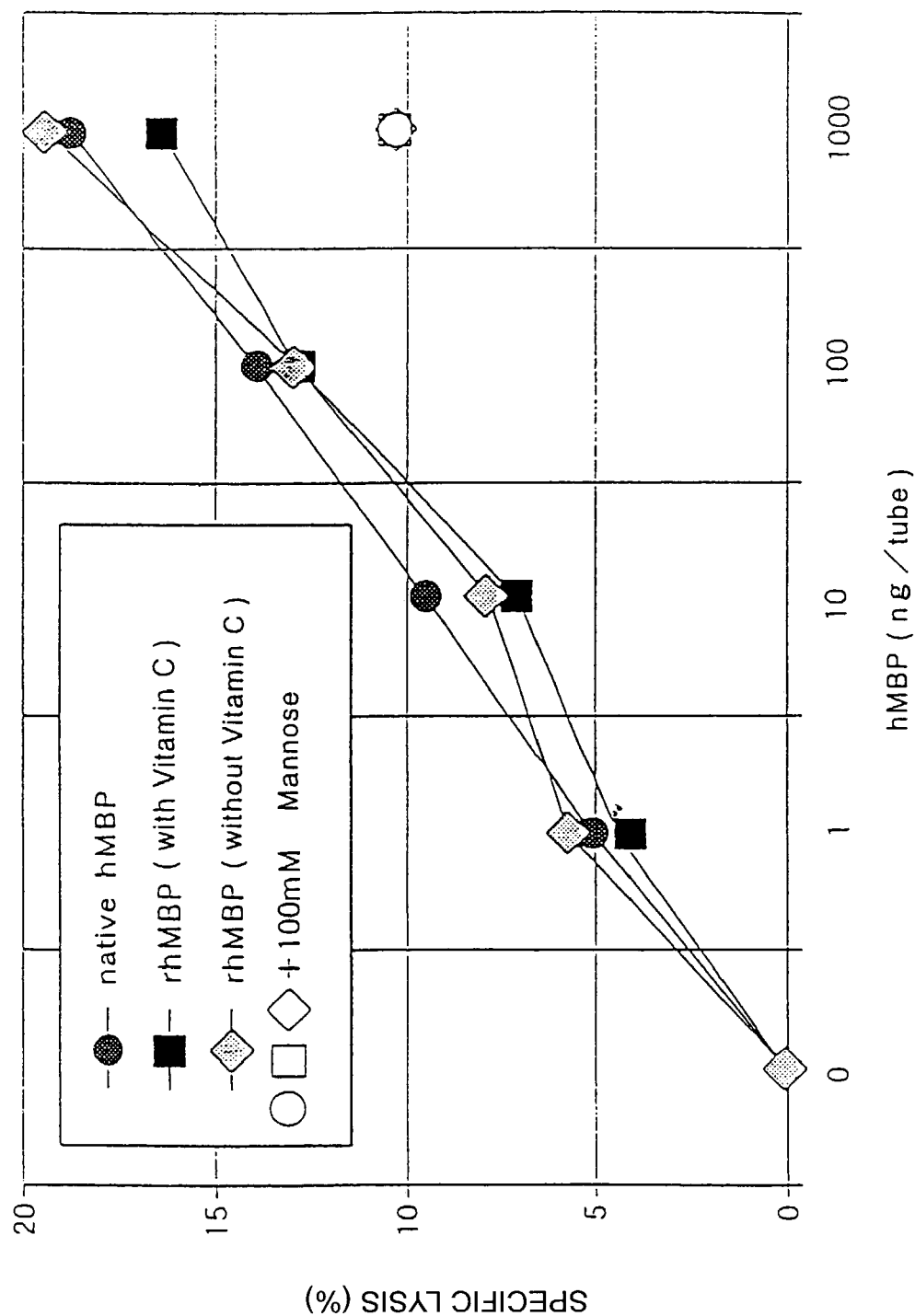
FIG. 22 is a graph showing solubility of Sheep Erythrocyte sensitized with rhMBP

Results thereof are shown in FIG. 22. As shown in FIG. 22, rhMBP (cultured with or without vitamin C) hemolyzed concentration-dependently sensitized sheep erythrocyte substantially like the native hMBP.

In view of this fact, it is deduced that rhMBP binds to mannan at the surface of the sensitized sheep erythrocyte, then the complements are activated accordingly. These activities were suppressed by an addition of mannose.

[Industrial Applicability]

Accordingly, the present invention realizes means for the large-scale production of homogenous rhMBP which exhibits equivalent physiological activities to be offered by MBP obtained conventionally from living body with low yield. Since the present rhMBP have similar physiological activities to be offered by the native hMBP, they will offer the various effects including an application thereof to the medicine field.

What is claimed is:

1. A method for producing a Recombinant Human Mannan-Binding Protein (rhMBP) comprising:
    (a) introducing expression vector pNOW1-hMBP into a Chinese Hamster Ovary (CHO) cell, wherein the CHO cell lacks dihydrofolate reductase;
    (b) culturing the CHO cell in a culture medium containing neomycin;
    (c) culturing the CHO cell in a culture medium containing methotrexate; and
    (d) collecting the rhMBP from the cultured CHO cell possessing resistance to both neomycin and methotrexate,
    wherein the expression vector pNOW1-hMBP comprises the plasmid pNOW1 and cDNA consisting of the nucleotide sequence of SEQ ID NO:2.

2. The method according to claim 1, wherein said rhMBP has a peak molecular weight of about 1,000 kDa–about 1,300 kDa as determined by 280 nm absorbance in gel-filtration chromatography.

3. The method according to claim 1, wherein said rhMBP has dual peak molecular weights of about 1,000 kDa–about 1,300 kDa and about 200 kDa–about 400 kDa as determined by 280 nm absorbance in gel-filtration chromatography.

* * * * *

UNITED STATES PATENT AND TRADEMARK OFFICE
CERTIFICATE OF CORRECTION

| | |
|---|---|
| PATENT NO. | : 7,049,099 B2 |
| APPLICATION NO. | : 10/054536 |
| DATED | : May 23, 2006 |
| INVENTOR(S) | : Nobutaka Wakamiya |

Page 1 of 1

It is certified that error appears in the above-identified patent and that said Letters Patent is hereby corrected as shown below:

On the Title Page:

Item (75), "Ibaraki" should be -- Ibaraki-shi, Osaka --.

In the Claims:

Column 46, lines 5-6, "a peak molecular weight of about 1,000 kDa - about 1,300" should be -- a specific peak at molecular weight of 1,000 kDa - 1,300 --.

Column 46, lines 9-10, "has dual peak molecular weights of about 1,000 kDa - about 1,300 kDa and about 200 kDa - about 400" should be -- has specific peaks at molecular weights of 1,000 kDa - 1,300 kDa and 200 kDa - 400 --.

Signed and Sealed this

Twenty-sixth Day of February, 2008

JON W. DUDAS
*Director of the United States Patent and Trademark Office*